US012734508B1

(12) United States Patent
Tahir

(10) Patent No.: US 12,734,508 B1
(45) Date of Patent: Sep. 15, 2026

(54) SYNTHESIS OF ZINC / TITANIUM MONOLITHIC PHOTOCATALYSTS AND APPLICATIONS THEREOF

(71) Applicant: United Arab Emirates University, Al Ain (AE)

(72) Inventor: Muhammad Tahir, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 19/080,221

(22) Filed: Mar. 14, 2025

(51) Int. Cl.

| | |
|---|---|
| ***B01J 23/80*** | (2006.01) |
| ***B01J 21/06*** | (2006.01) |
| ***B01J 35/39*** | (2024.01) |
| ***B01J 35/57*** | (2024.01) |
| ***B01J 37/02*** | (2006.01) |
| ***B01J 37/04*** | (2006.01) |
| ***B01J 37/06*** | (2006.01) |
| ***B01J 37/08*** | (2006.01) |
| ***C01B 3/326*** | (2026.01) |
| ***C01B 32/40*** | (2017.01) |
| ***C07C 1/12*** | (2006.01) |
| ***C07C 1/22*** | (2006.01) |

(52) U.S. Cl.
CPC ............ *B01J 23/80* (2013.01); *B01J 21/063* (2013.01); *B01J 35/39* (2024.01); *B01J 35/57* (2024.01); *B01J 37/0215* (2013.01); *B01J 37/0236* (2013.01); *B01J 37/04* (2013.01); *B01J 37/06* (2013.01); *B01J 37/084* (2013.01); *C01B 3/326* (2013.01); *C01B 32/40* (2017.08); *C07C 1/12* (2013.01); *C07C 1/22* (2013.01); *C01B 2203/1023* (2013.01); *C01B 2203/1052* (2013.01); *C01B 2203/1076* (2013.01); *C01B 2203/1082* (2013.01); *C01B 2203/1223* (2013.01)

(58) Field of Classification Search
CPC . B01J 23/80; B01J 21/063; B01J 35/57; B01J 35/39; B01J 37/0215; B01J 37/0236; B01J 37/04; B01J 37/06; B01J 37/084; C01B 3/326; C01B 32/40; C07C 1/12; C07C 1/22
See application file for complete search history.

(56) References Cited

FOREIGN PATENT DOCUMENTS

CN 104209110 A * 12/2014

OTHER PUBLICATIONS

Gnanasekaran et al., Environmental Research, (2024), v.258, p. 119441(1-10).*
Anucha et al., Chem. Engin. Journal Adv., (2022), v. 10, p. 100262(1-16).*
Zheng et al., Materials Today Chemistry, (2024), v.36, 101928(1-25).*
Chen et al., Coatings, (2022), v.12, 1407(1-18).*
Chandrasekaran et al., J of Material Chemistry A, (2018), 6(24), 11078-11104.*
Zhang et al., Sensor & Actuators B Chemical, (2020), v.321, p. 128461(1-10).*

* cited by examiner

*Primary Examiner* — Yong L Chu
(74) *Attorney, Agent, or Firm* — MH2 Technology Law Group, LLP

(57) ABSTRACT

According to a first aspect of the present invention, there is provided a photocatalytic composite. The photocatalytic composite comprises zinc cobalt oxide nanorods ($ZnCo_2O_4$ NRs); and titanium dioxide ($TiO_2$), wherein said photocatalytic composite has a monolithic structure. According to a second aspect of the present invention, there is provided a method of manufacturing a monolithic $ZnCo_2O_4/TiO_2$ composite. The method comprises the steps of: obtaining $ZnCo_2O_4$ nanorods; obtaining a titanium dioxide sol-gel precursor; mixing the $ZnCo_2O_4$ nanorods and the titanium dioxide sol-gel precursor to form a $ZnCo_2O_4/TiO_2$ sol; obtaining a monolith substrate; and forming a monolithic $ZnCo_2O_4/TiO_2$ composite from the $ZnCo_2O_4/TiO_2$ sol and the monolith substrate using a sol-gel-dip coating method. According to a third aspect of the present invention, there is provided the use of a photocatalytic composite according to the present invention for photocatalytic reduction of $CO_2$. According to a fourth aspect of the present invention, there is provided a method of photocatalytic reduction of CO2 using a photocatalytic composite, comprising the steps of: obtaining a monolithic $ZnCo_2O_4/TiO_2$ composite; and reducing $CO_2$ using the monolithic $ZnCo_2O_4/TiO_2$ composite.

6 Claims, 25 Drawing Sheets

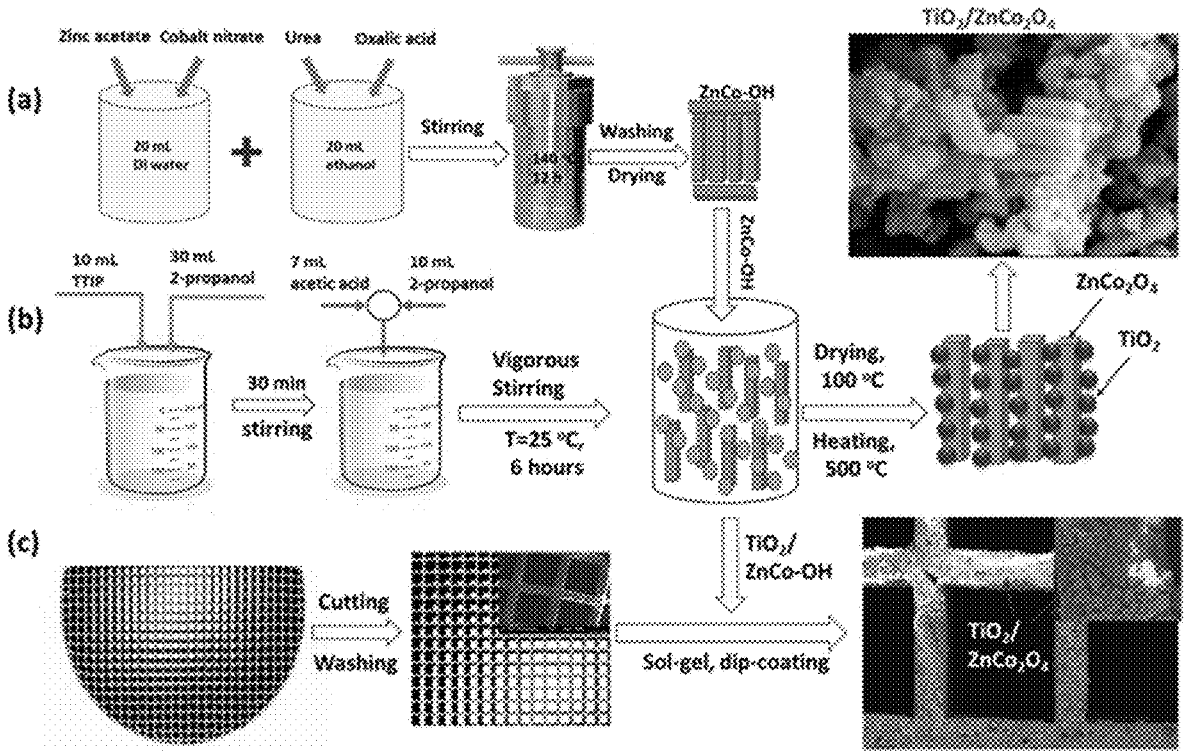
FIGURES 1 (A-C)

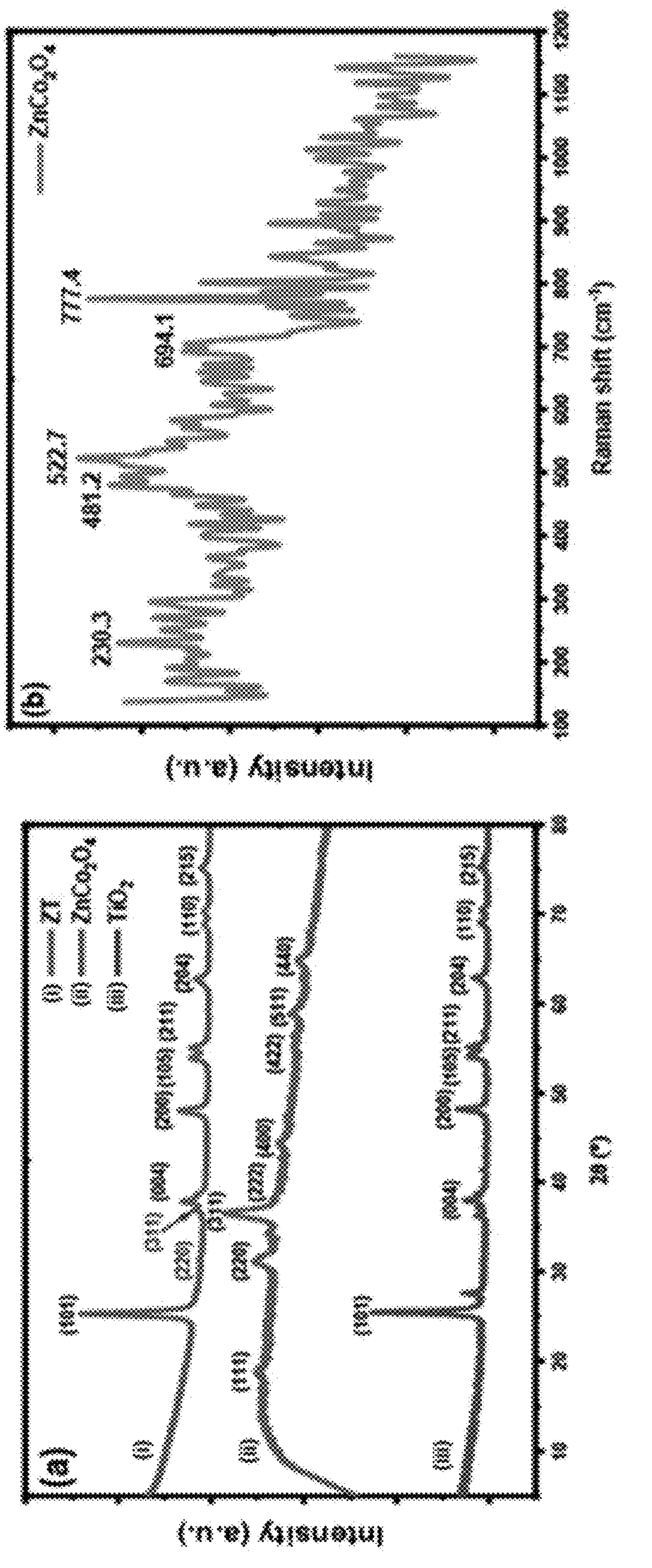
FIGURES 2(A-B)

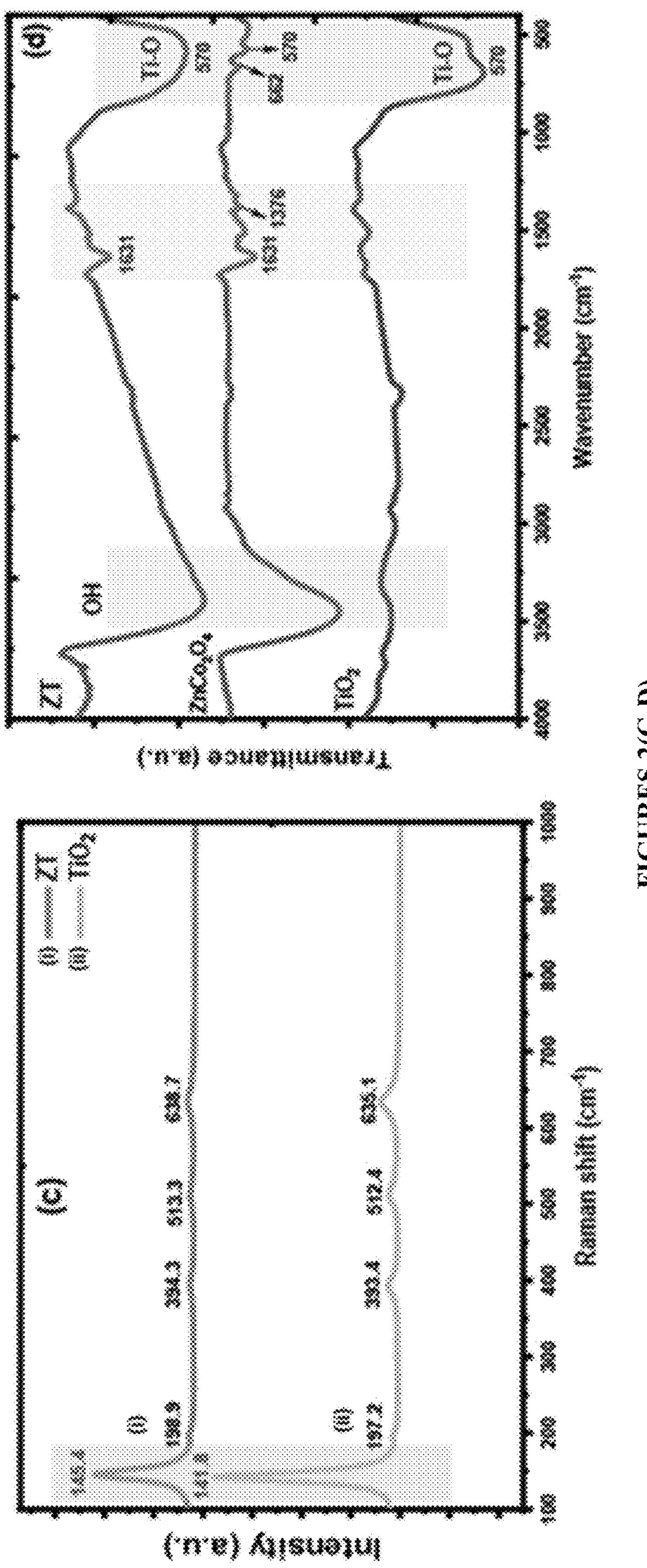
FIGURES 2(C-D)

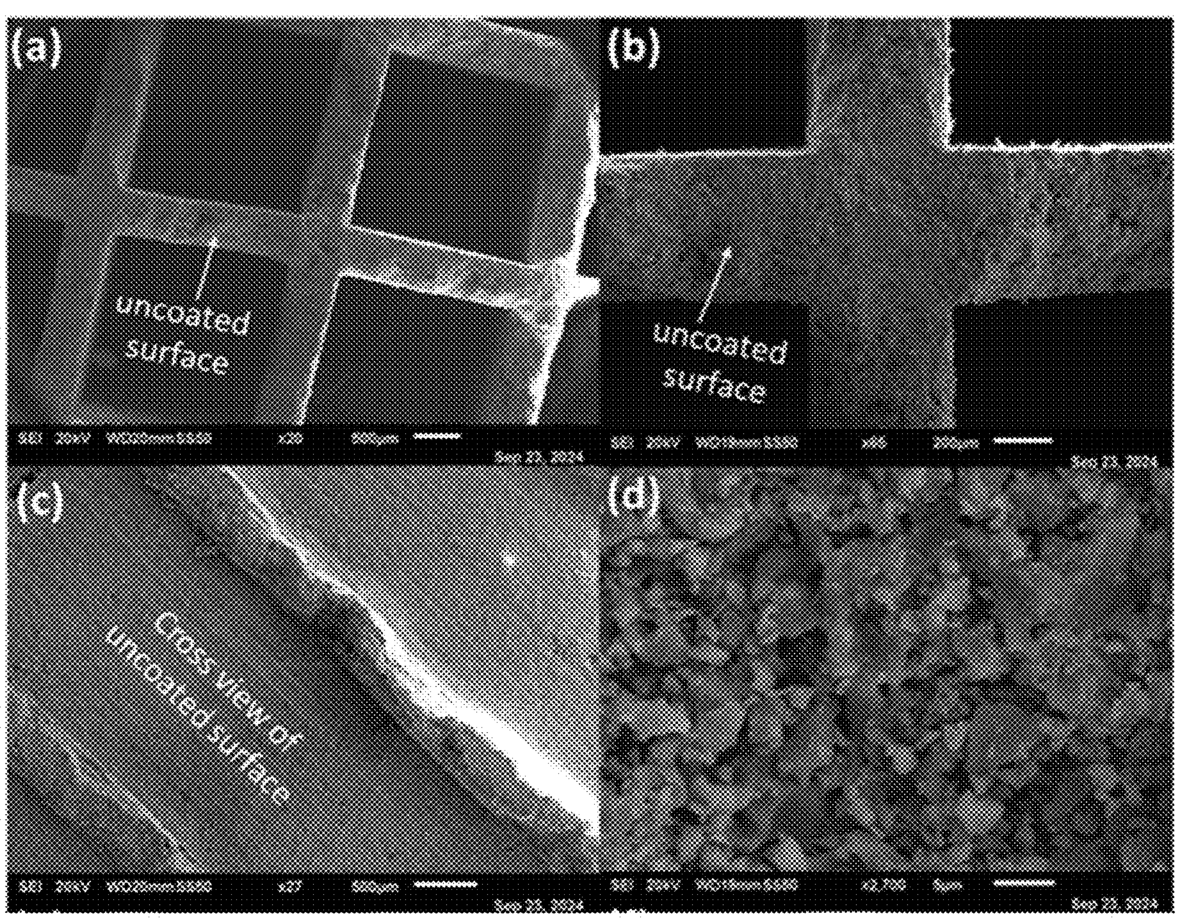
FIGURES 3(A-D)

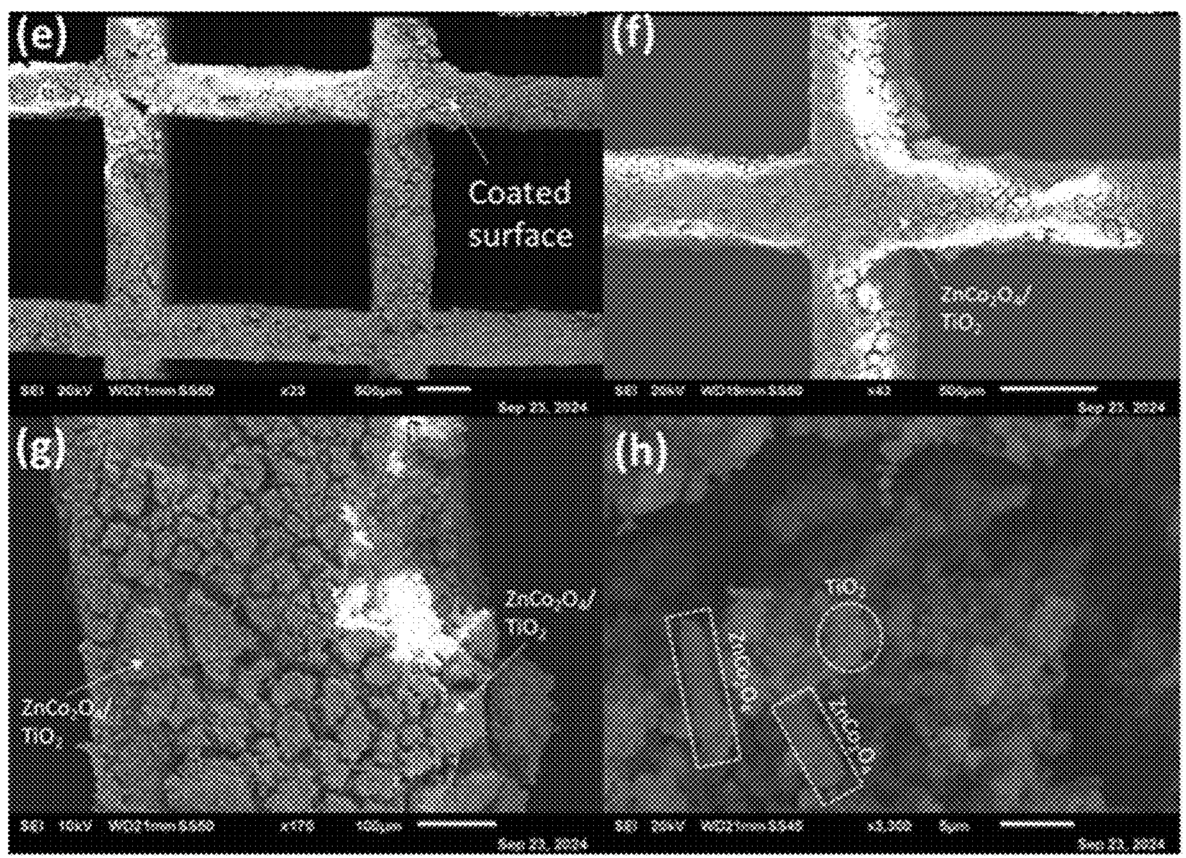
FIGURES 3 (E-F)

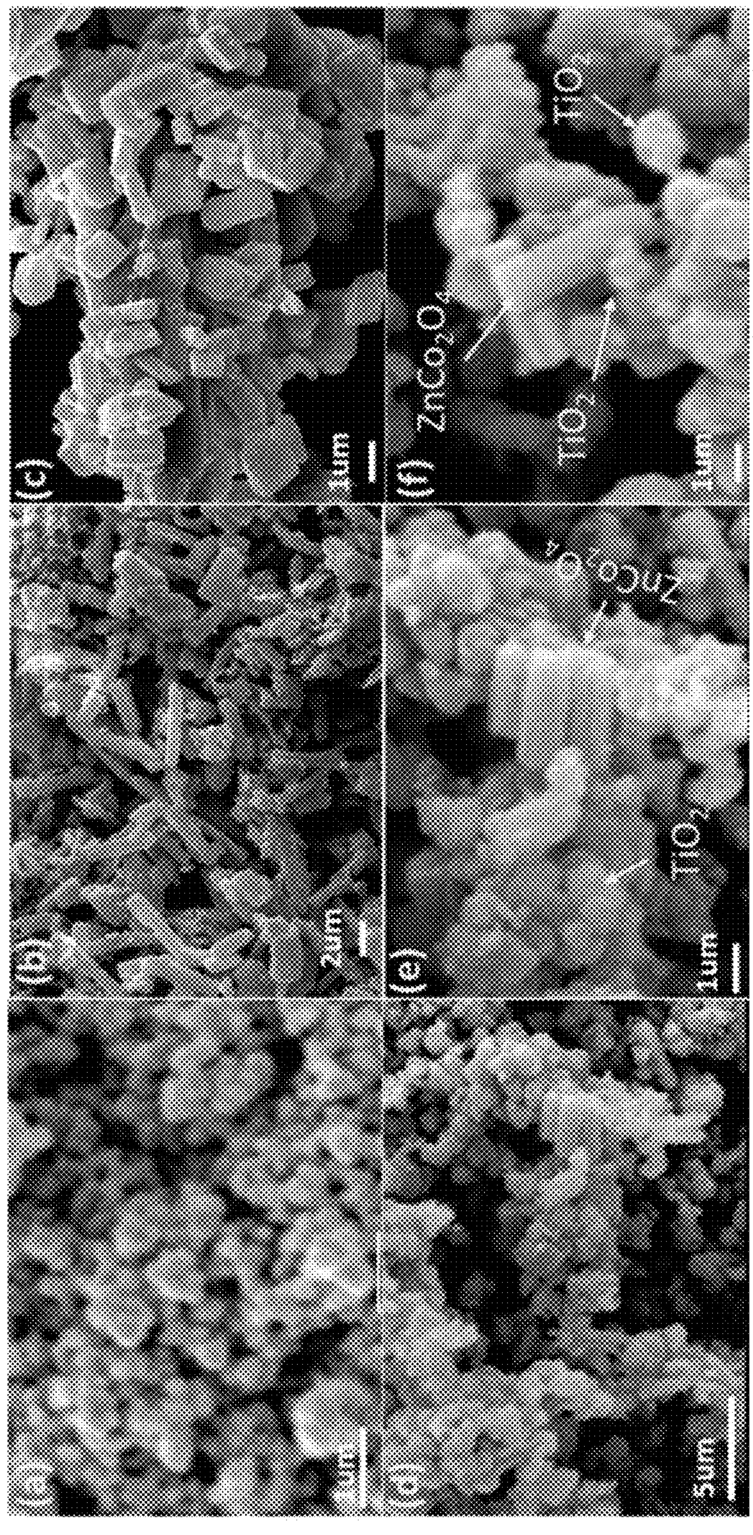
FIGURES 4 (A-F)

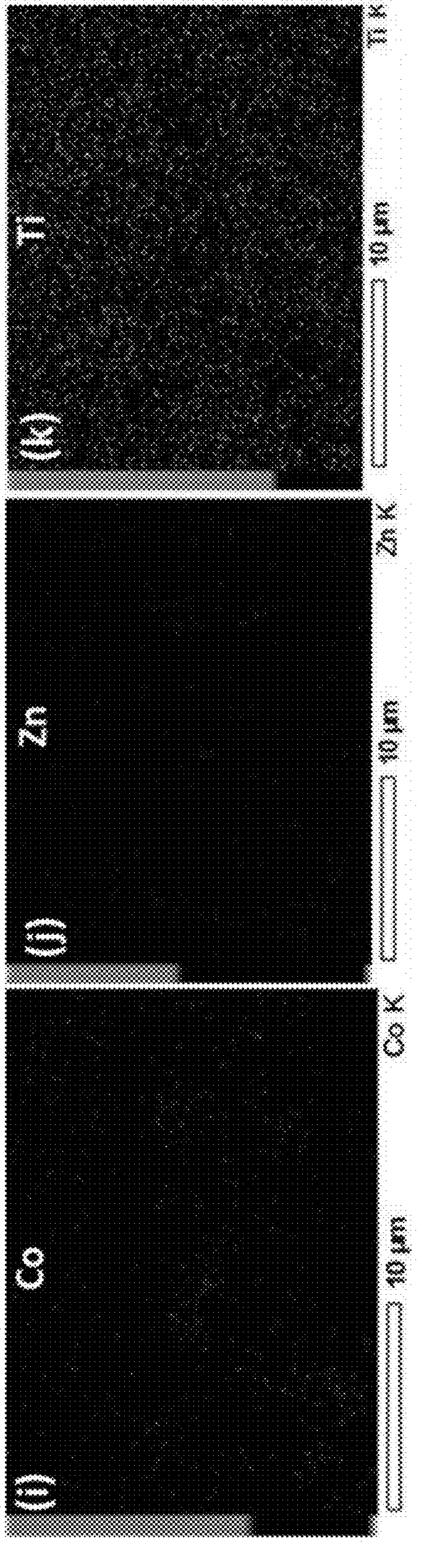
FIGURES 4 (I-K)composite

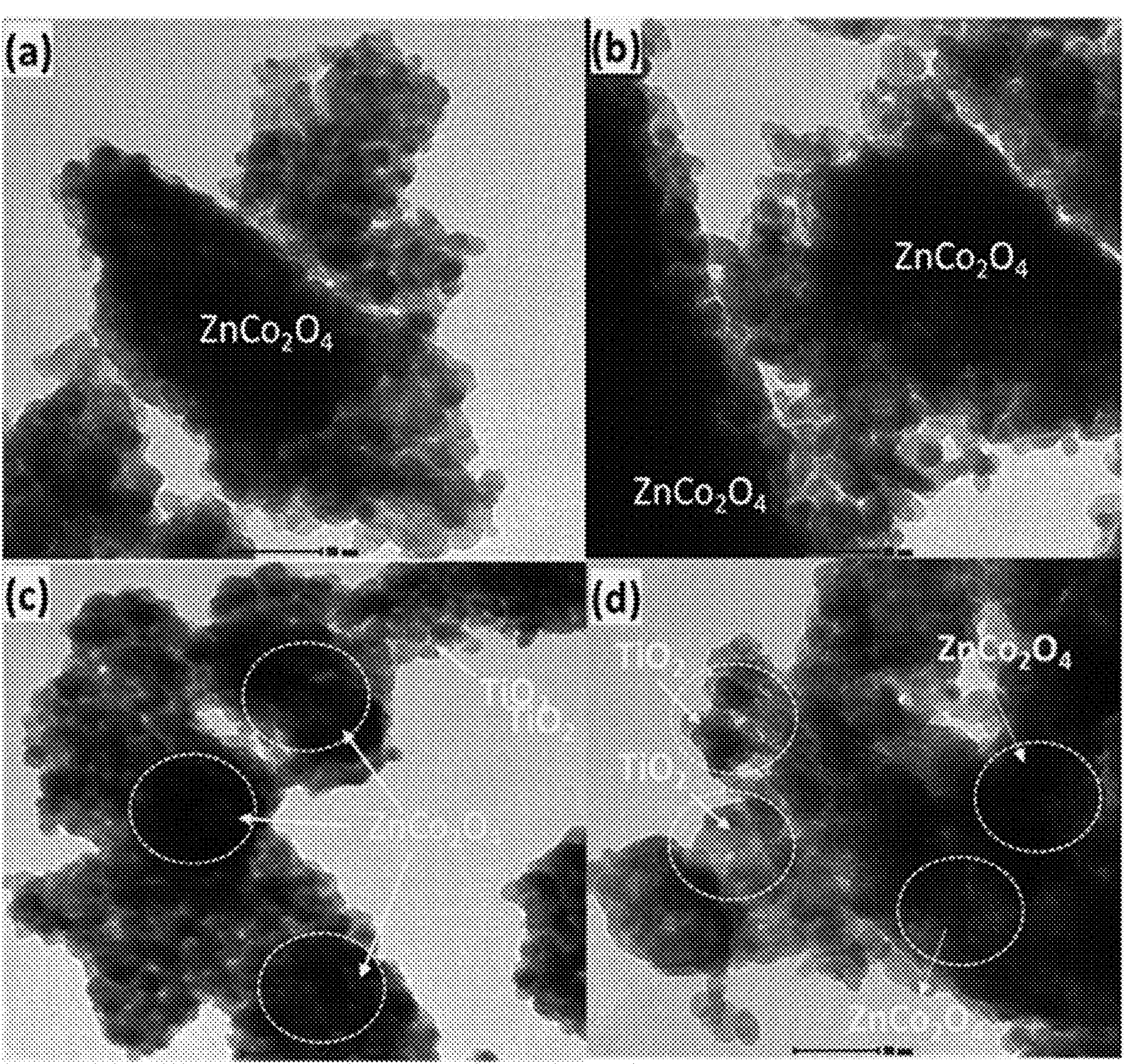
FIGURES 5 (A-D)

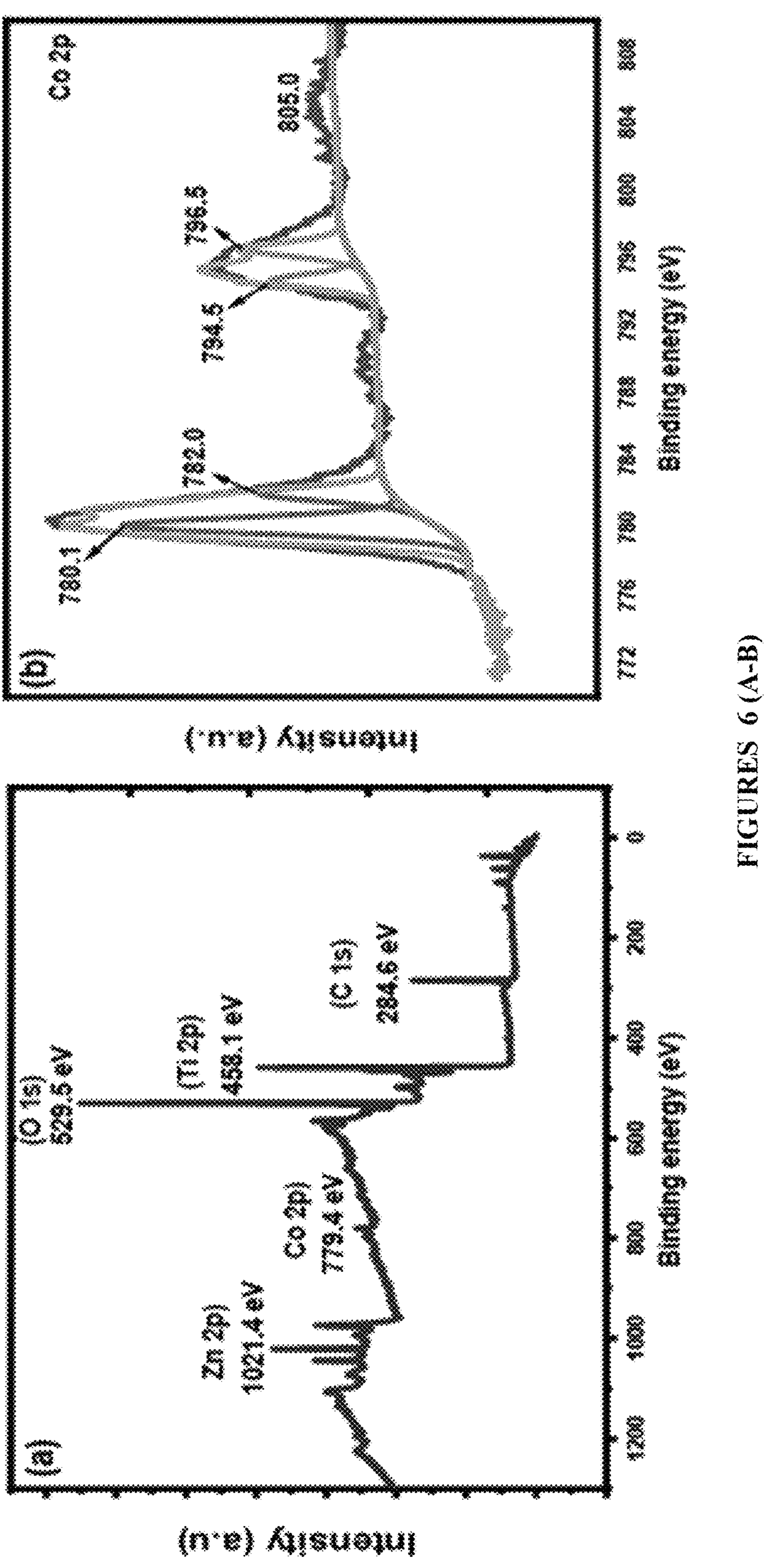
FIGURES 6 (A-B)

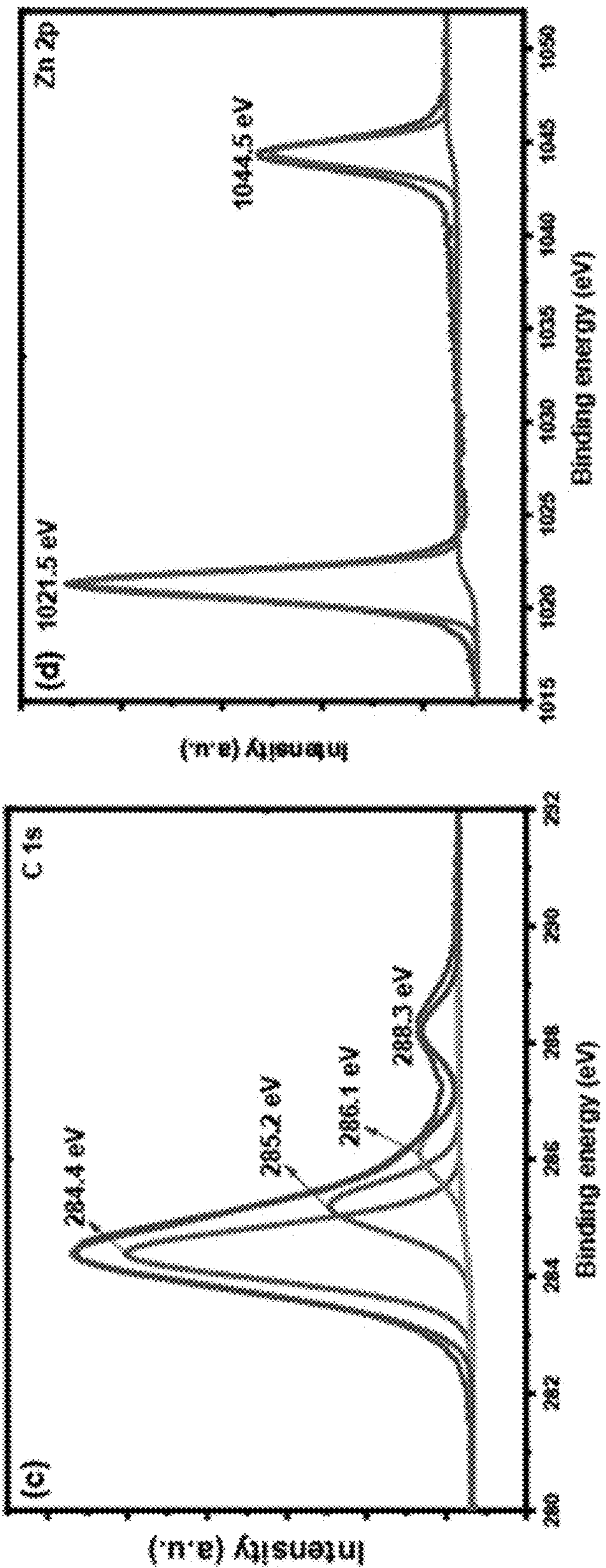
FIGURES 6 (C-D)

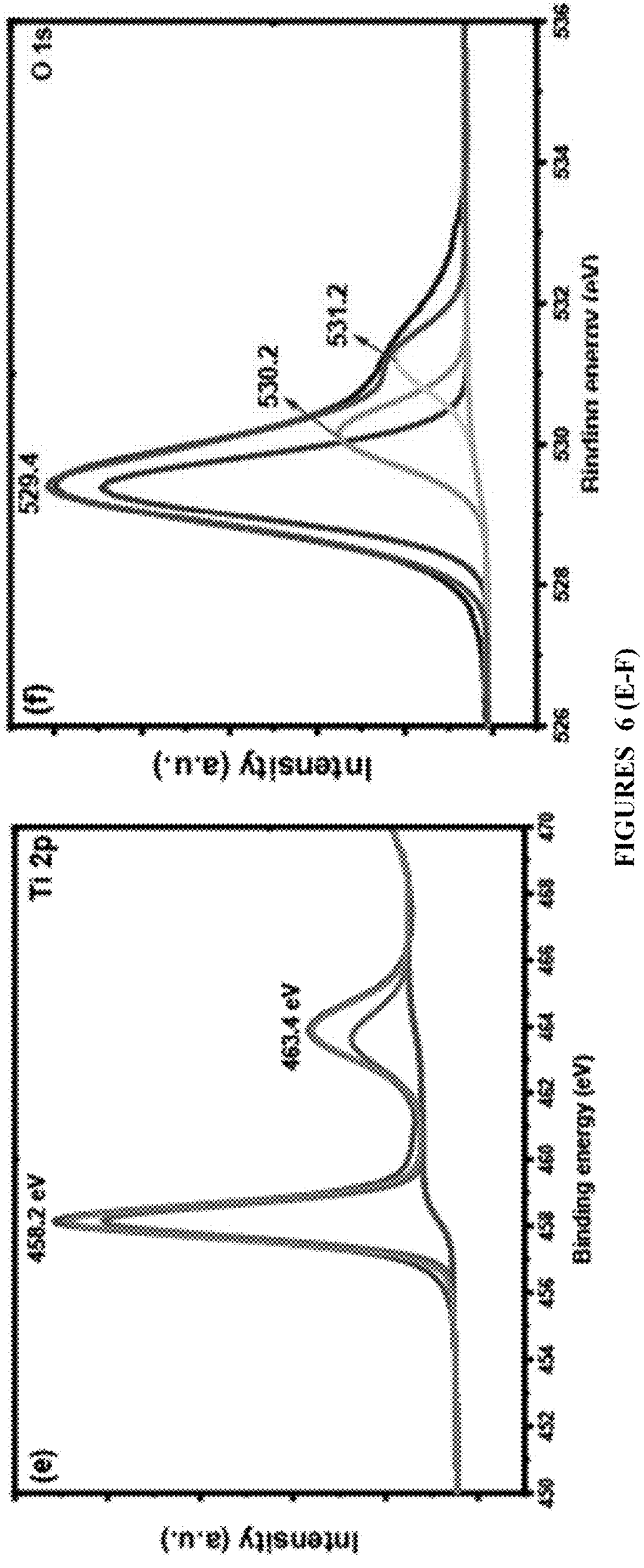
FIGURES 6 (E-F)

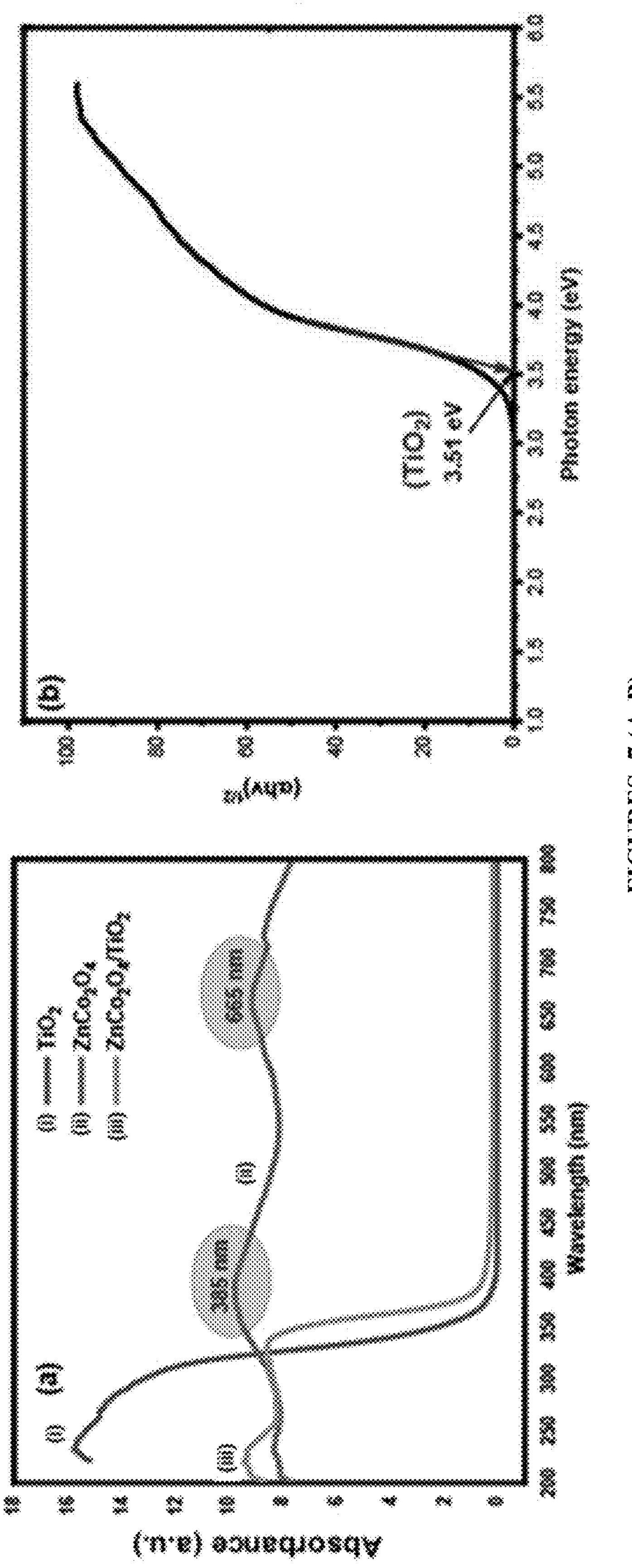
FIGURES 7 (A-B)

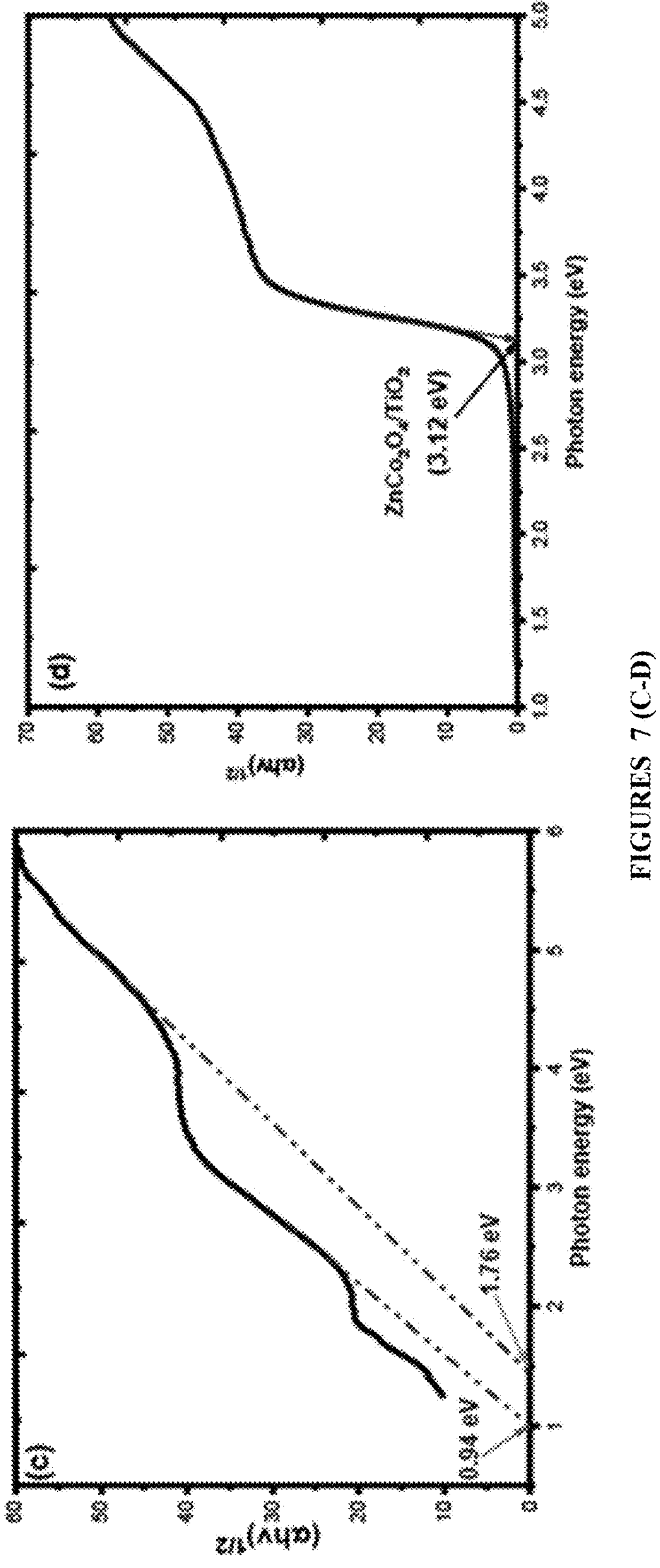
FIGURES 7 (C-D)

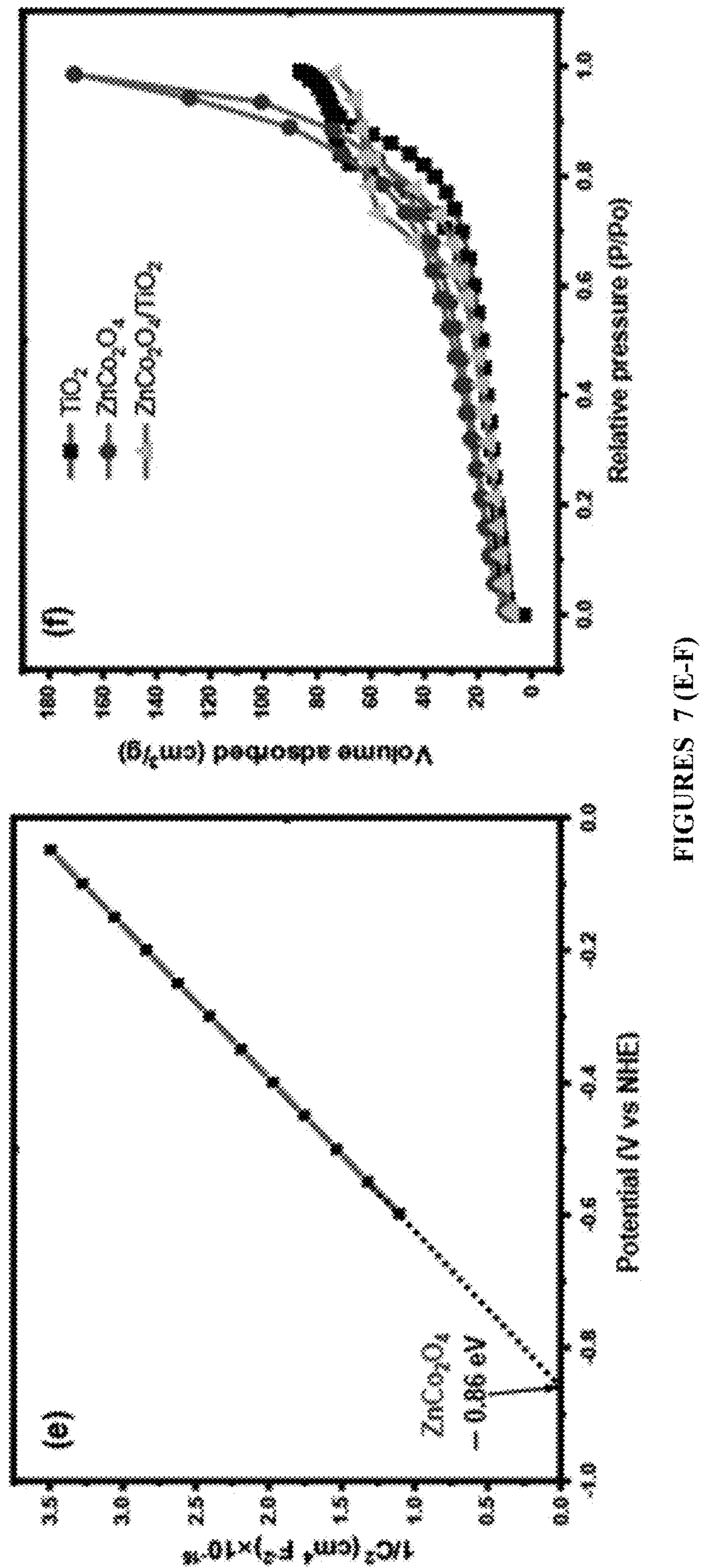
FIGURES 7 (E-F)

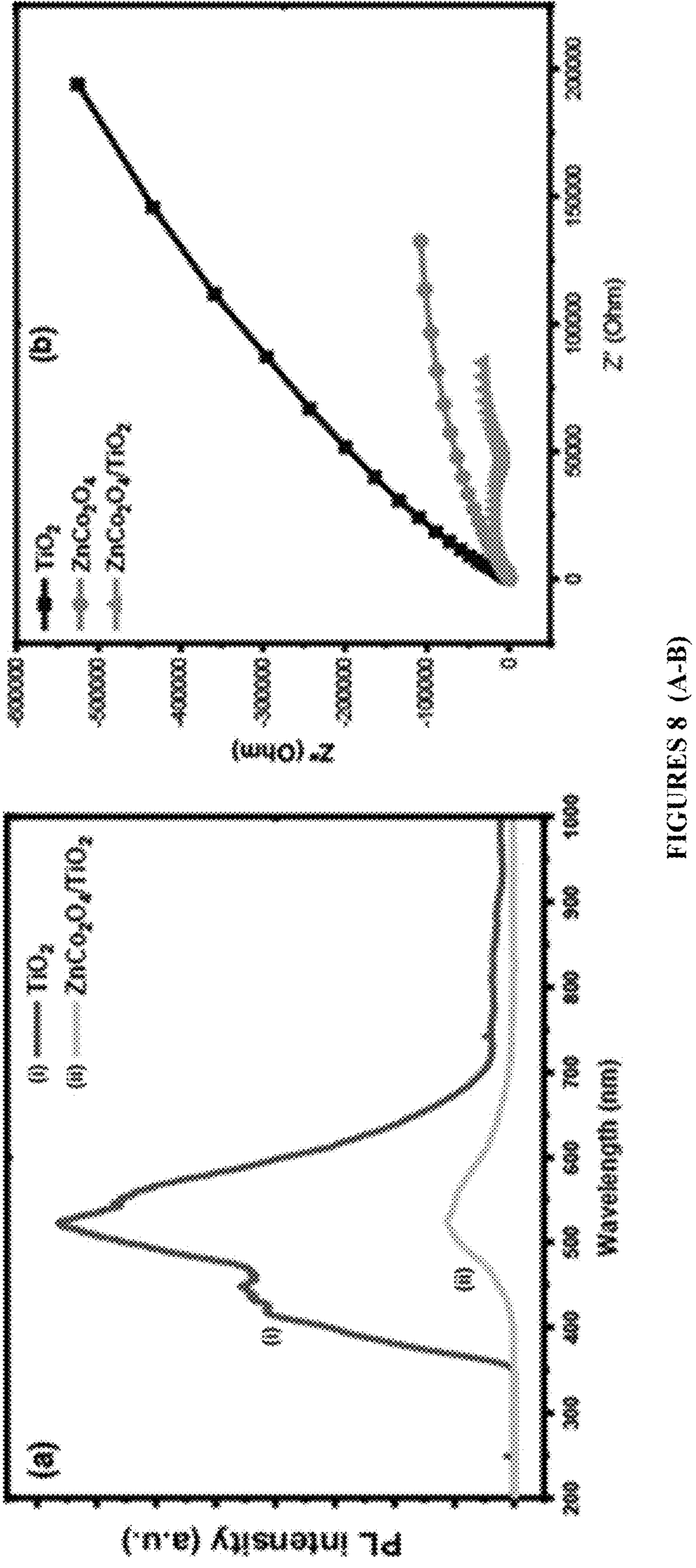
FIGURES 8 (A-B)

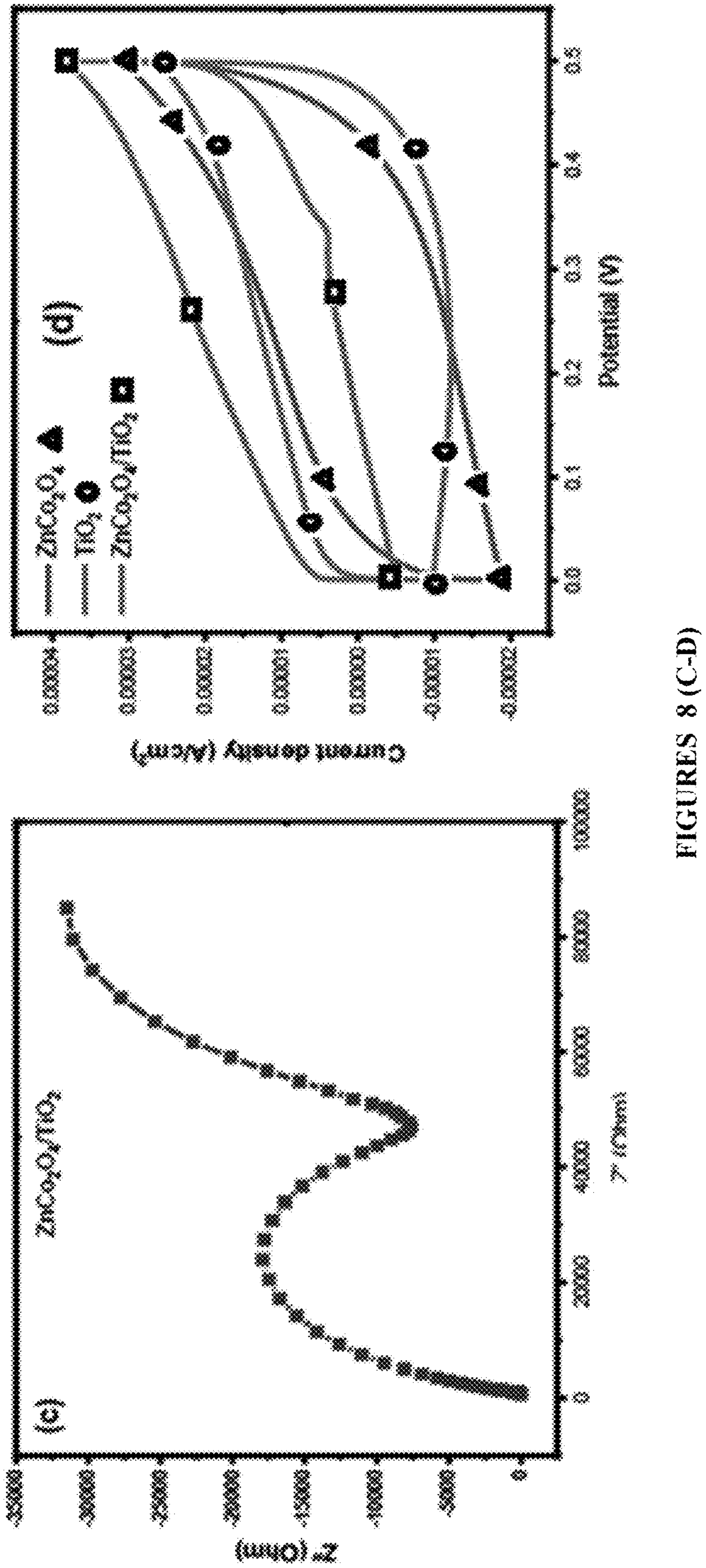
FIGURES 8 (C-D)

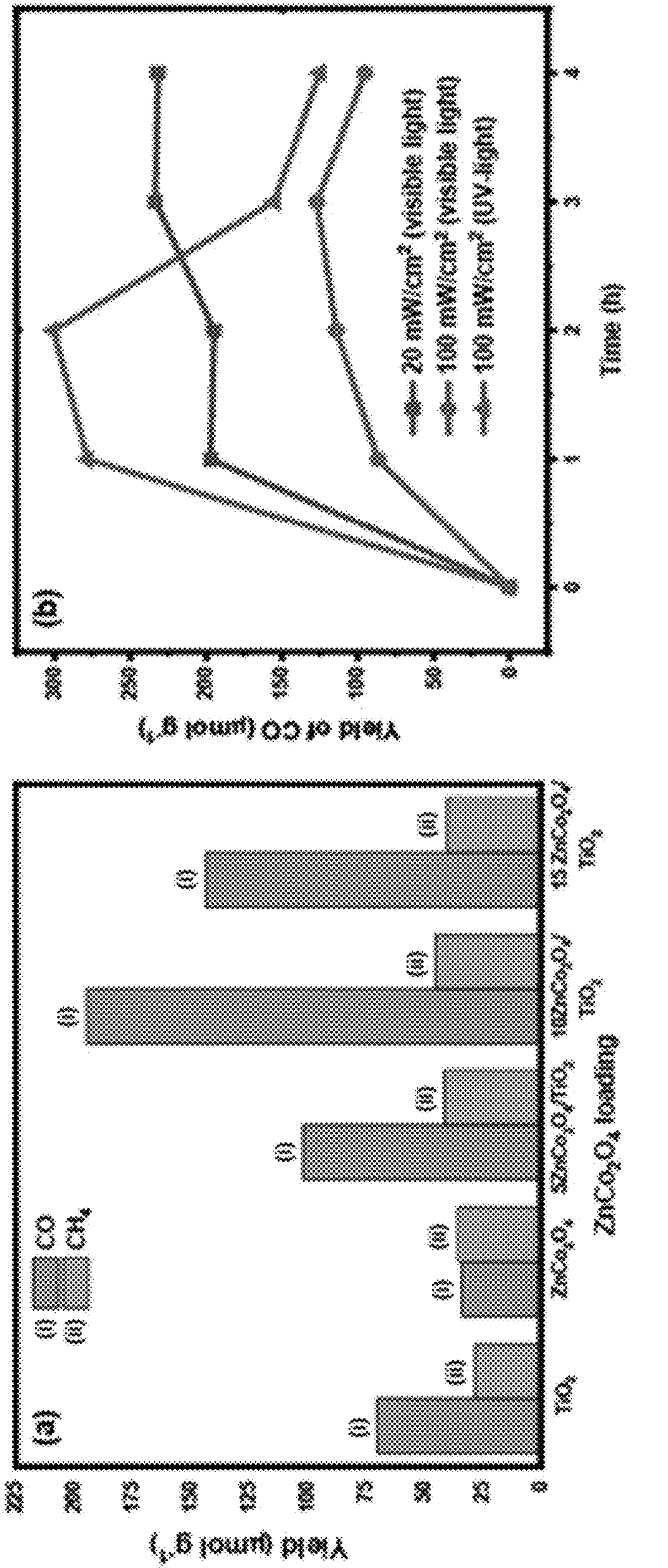
FIGURES 9 (A-B)

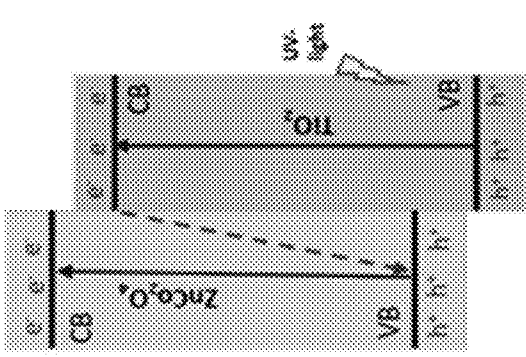
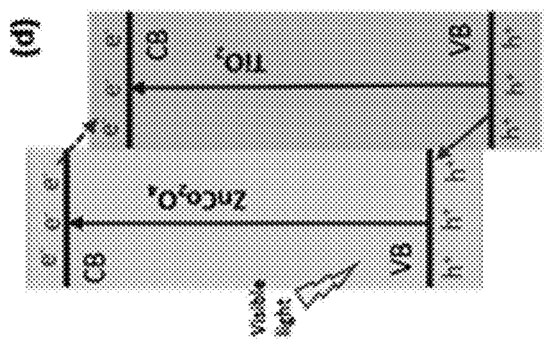
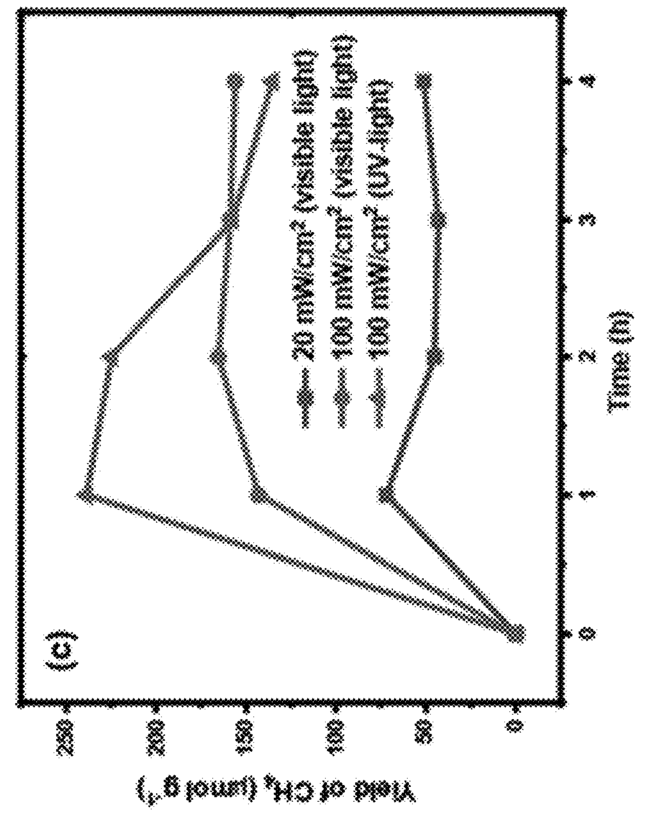
FIGURES 9 (C-D)

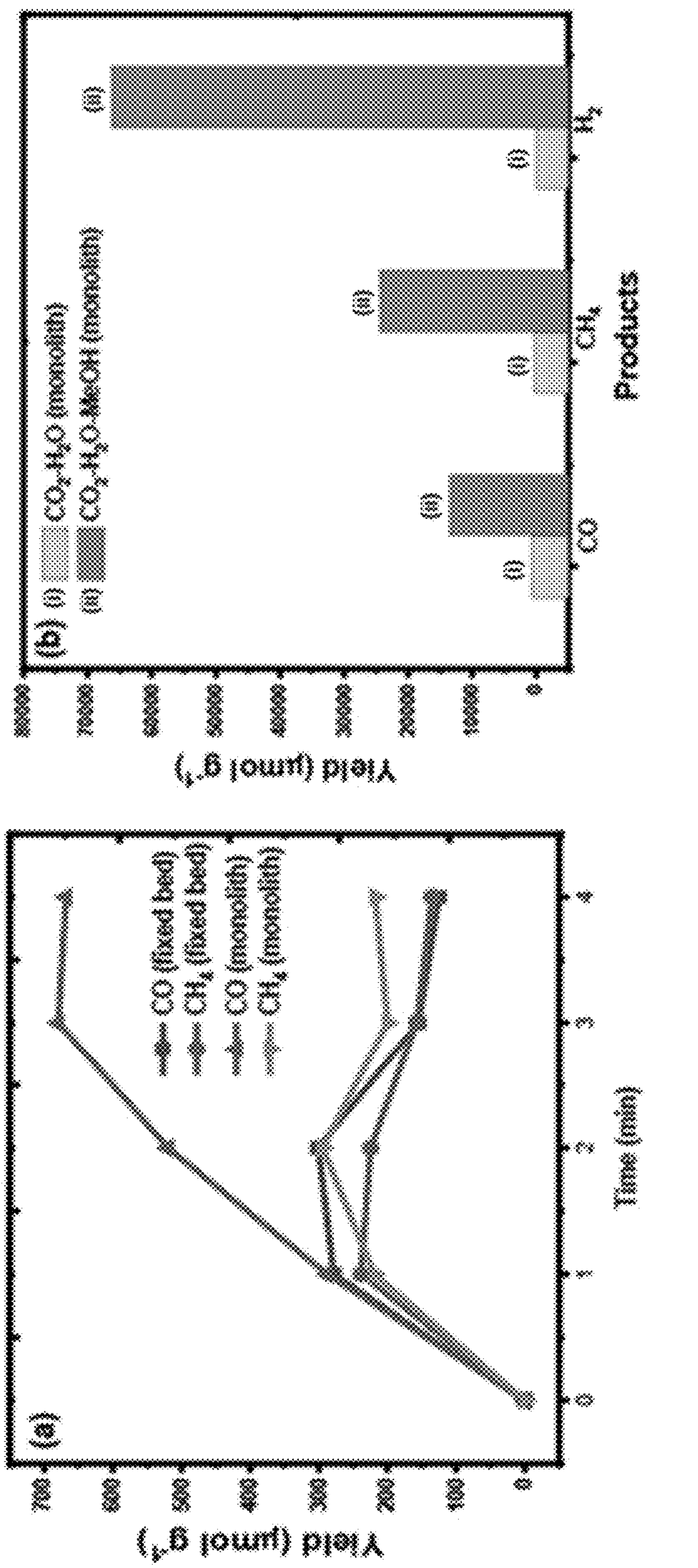
FIGURES 10 (A-B)

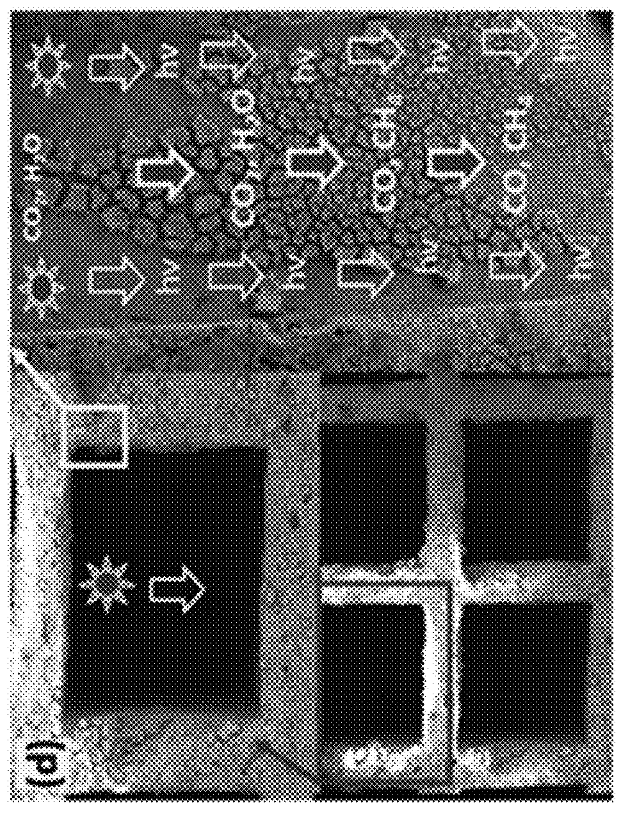
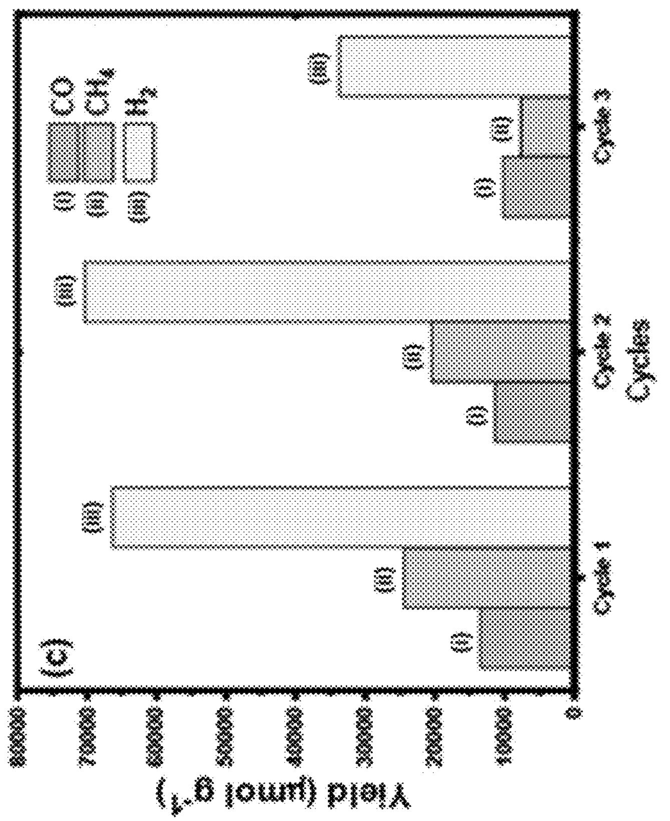
FIGURES 10 (C-D)

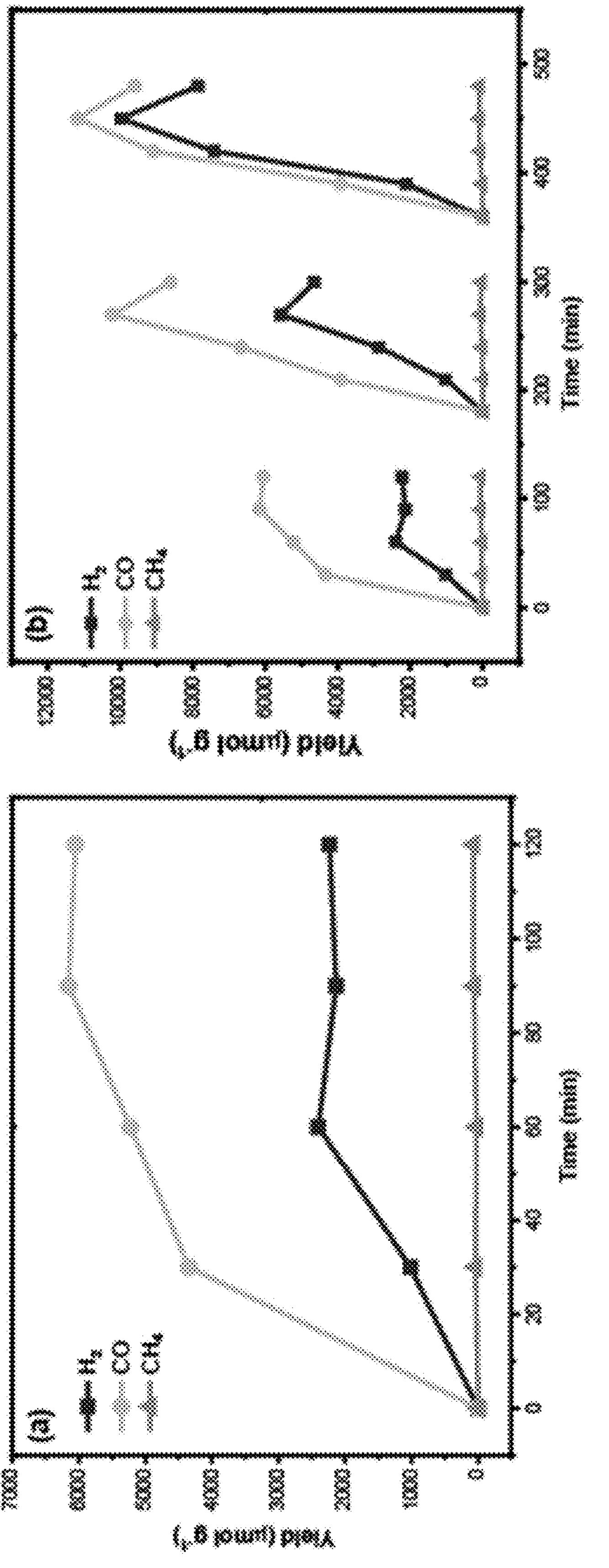
FIGURES 11 (A-B)

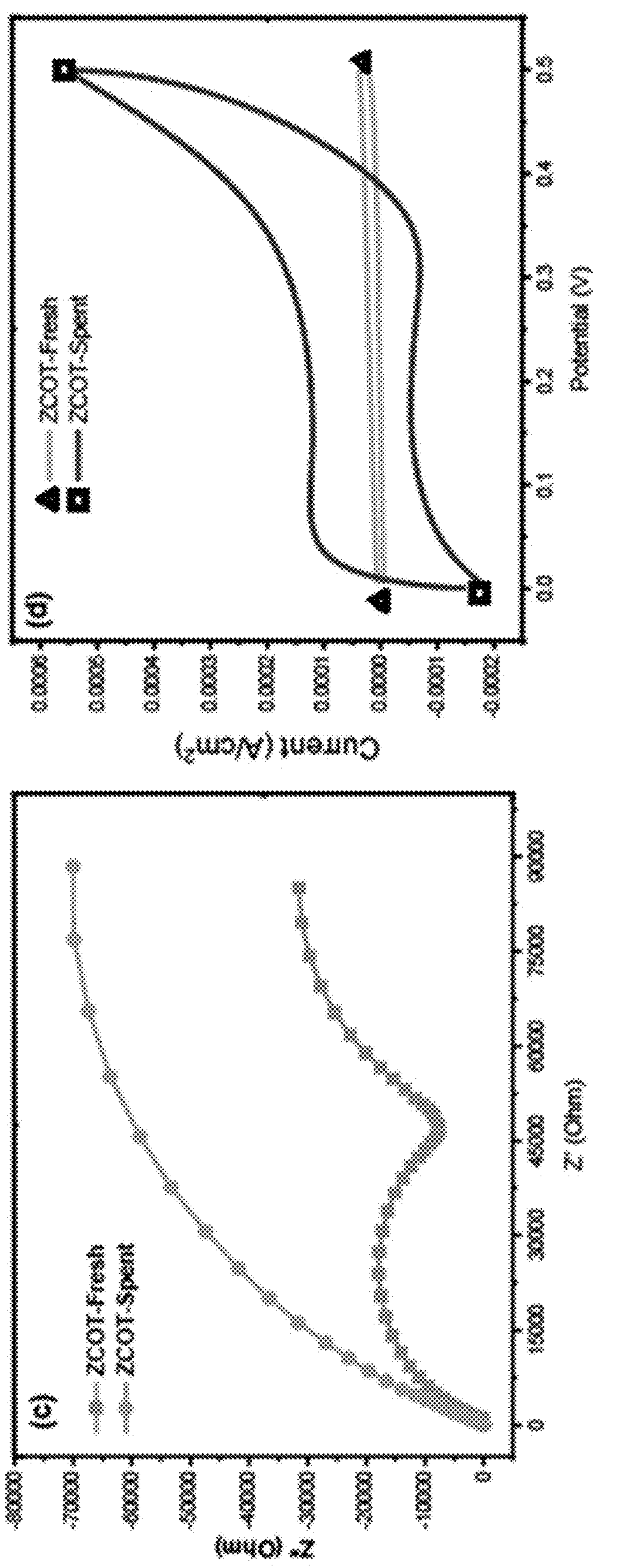
FIGURES 11 (C-D)

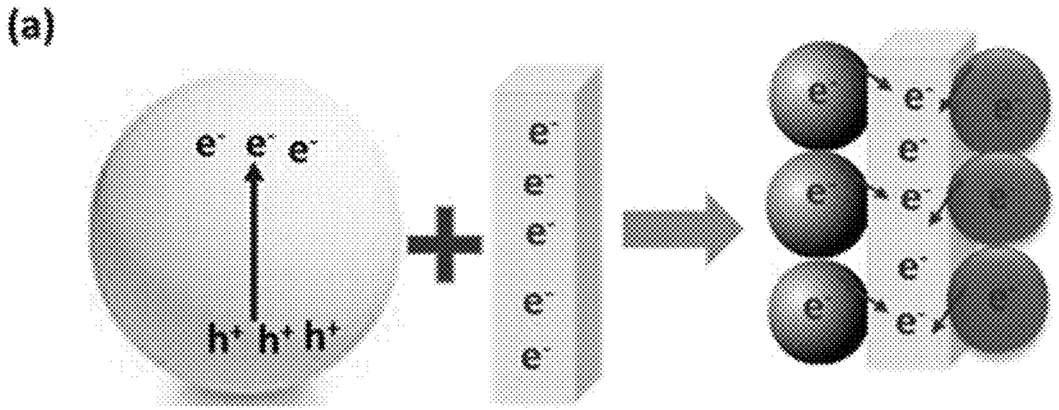
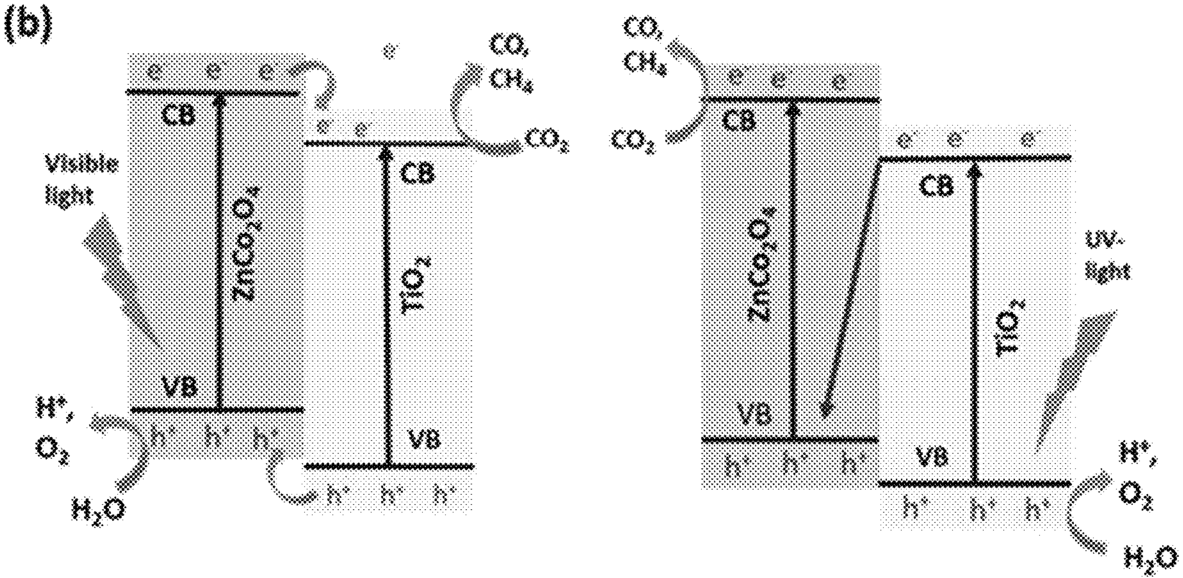
FIGURES 12 (A-B)

SYNTHESIS OF ZINC / TITANIUM MONOLITHIC PHOTOCATALYSTS AND APPLICATIONS THEREOF

FIELD OF THE INVENTION

The present invention relates to the field of photocatalytic $CO_2$ reduction, including efficiently converting $CO_2$ into valuable products such as carbon monoxide (CO), methane ($CH_4$), and hydrogen ($H_2$) under UV and visible light irradiation. The present invention also relates to the synthesis of zinc/titanium monolithic photocatalysts and applications thereof.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Extensive fossil fuel use has significantly increased atmospheric $CO_2$ levels. Greenhouse gases are significant contributors to climate change. Carbon dioxide ($CO_2$), a prominent greenhouse gas, significantly contributes to climate change by trapping heat in the atmosphere, leading to global warming and associated environmental disruptions. The primary sources of $CO_2$ emissions are human activities such as the combustion of fossil fuels (coal, oil, and natural gas) for energy, industrial processes, deforestation, and certain agricultural practices. In response to this pressing issue, climate action involves efforts to mitigate greenhouse gas emissions, adapt to climate change impacts, and transition to a low-carbon economy. It encompasses various strategies at local, national, and international levels to reduce $CO_2$ emissions and limit global temperature rise. According to the United Nations (UN) sustainable development goals (SDGs), a global temperature should not exceed 1.5° C. to achieve sustainability. Thus, the conversion of $CO_2$ into valuable chemicals and fuels through photocatalysis is a promising approach to addressing climate change and advancing sustainability.

Developing innovative materials and methods for $CO_2$ mitigation, particularly through phototechnology, presents a promising solution by converting $CO_2$ into valuable fuels, paving the way toward net-zero emissions. Spinel-type multimetal oxides have recently garnered significant attention as high-performance semiconductor materials due to their ability to exhibit multiple oxidation states, superior electrochemical performance, and improved electrical conductivity. In particular, the spinel cobaltites ($MCo_2O_4$) family have been extensively researched due to their ability to enhance photocatalytic performance. Cobalt-based metal oxides exhibit unique properties, such as increased electronic conductivity, making them a promising choice for photocatalytic applications. A variety of cations can be combined to form multimetallic spinel oxides.

Transition metal oxides, incorporating multiple metals like zinc (Zn), can potentially enhance stability and photocatalytic efficiency. Constructing $ZnCo_2O_4$ as a semiconductor has increased because of structural stability and higher conductivity For example, $ZnCo_2O_4$ coupled with inorganic salt was promising for the utilization of $CO_2$ and can used in $CO_2$ reduction applications. Similarly, $ZnCo_2O_4$ quantum dots (QDs) coupled with $g\text{-}C_3N_4$ have shown great potential for maximising hydrogen production. The quantum size effect in $ZnCo_2O_4$ quantum dots (QDs) leads to a significant broadening of the electronic bandgap. This increase in bandgap width elevates the energy of electrons in the conduction band and holes in the valence band, thereby enhancing the material's catalytic efficiency for hydrogen generation reactions. In another development, the $ZnCo_2O_4/g\text{-}C_3N_4$ composite was investigated for photodegradation of MB and significantly higher photocatalytic efficiency was achieved. Extensive research has been conducted on mixed transition metal oxide-based materials for efficient photocatalytic $CO_2$ reduction reactions.

However, there remains a need for a photocatalyst which can significantly enhance its photocatalytic efficiency and selectivity while maintaining low cost and excellent stability. There also remains a need for a method of synthesising a suitable photocatalyst. The present invention seeks to address at least some of these issues.

SUMMARY OF THE INVENTION

According to a first aspect of the present invention, there is provided a photocatalytic composite. The photocatalytic composite comprises zinc cobalt oxide nanorods ($ZnCo_2O_4$ NRs); and titanium dioxide ($TiO_2$), wherein said photocatalytic composite has a monolithic structure.

According to a second aspect of the present invention, there is provided a method of manufacturing a monolithic $ZnCo_2O_4/TiO_2$ composite. The method comprises the steps of: obtaining $ZnCo_2O_4$ nanorods; obtaining a titanium dioxide sol-gel precursor; mixing the $ZnCo_204$ nanorods and the titanium dioxide sol-gel precursor to form a $ZnCo_2O_4/TiO_2$ sol; obtaining a monolith substrate; and forming a monolithic $ZnCo_2O_4/TiO_2$ composite from the $ZnCo_2O_4/TiO_2$ sol and the monolith substrate using a sol-gel-dip coating method.

The present inventor has unexpectedly discovered a synergistic effect provided by the photocatalytic composite of the present invention, making it highly suitable for photocatalytic applications. Particularly, the combination of $TiO_2$ with $ZnCo_2O_4$ with the functional benefits of a monolithic structure provides improved light absorption, enhanced charge separation efficiency, and accelerated reaction kinetics. For example, the unexpected synergistic interaction between OD $TiO_2$ and 1D $ZnCo_2O_4$ provides a promising approach for enhancing charge transfer dynamics and optimizing photocatalytic activity. Additionally, the combination of $TiO_2$ with $ZnCo_2O_4$ significantly enhances photocatalytic efficiency and selectivity. This enhancement is achieved while maintaining a low-cost structure and ensuring excellent stability, making it a promising development for sustainable and cost-effective photocatalytic applications.

According to a third aspect of the present invention, there is provided the use of a photocatalytic composite according to the present invention for photocatalytic reduction of $CO_2$. The photocatalytic composite may be a photocatalytic composite according to the first aspect of the present invention.

According to a fourth aspect of the present invention, there is provided a method of photocatalytic reduction of CO2 using a photocatalytic composite, comprising the steps of: obtaining a monolithic $ZnCo_2O_4/TiO_2$ composite; and reducing $CO_2$ using the monolithic $ZnCo_2O_4/TiO_2$ composite.

The monolithic $ZnCo_2O_4/TiO_2$ composite may be the photocatalytic composite according to the first aspect of the present invention. The monolithic $ZnCo_2O_4/TiO_2$ composite may be obtained using the method of manufacturing a monolithic $ZnCo_2O_4/TiO_2$ composite according to the second aspect of the present invention.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

FIGS. 1 (A-C) illustrates (A) Synthesis of $ZnCo_2O_4$ (ZCO); (B) Synthesis of $ZnCo_2O_4/TiO_2$ (ZCOT); and (C) Synthesis of monolithic $ZnCo_2O_4/TiO_2$, in accordance with the present invention.

FIGS. 2 (A-D) depict (A) XRD patterns of $TiO_2$, ZCO and ZCOT (ZT); Raman spectra of ZCO; (C) Raman spectra of ZCOT (ZT) composite; and (D) FTIR analysis of ZCO, $TiO_2$ and ZCOT (ZT) composite, in accordance with the present invention.

FIGS. 3(A-H)—depict SEM analysis of bare monoliths: (A-B) Uncoated monolith channels; (C) cross-view of uncoated channel surface; (D) Morphology of bare monolith surface; and SEM analysis of coated monoliths: (E-F) coated monolith channels; (G) Coated channel with thin film of catalyst; and (H) morphology of $ZnCo_2O_4/TiO_2$ over the channel surface, in accordance with the present invention.

FIGS. 5 (A-D)—depict TEM analysis of $ZnCo_2O_4/TiO_2$: (A-B) TEM images of $ZnCo_2O_4/TiO_2$ composite; and (C-D) HRTEM images of $ZnCo_2O_4/TiO_2$ composite with their good interface interaction, in accordance with the present invention.

FIGS. 6 (A-F)—depict High-resolution XPS spectra of $ZnCo_2O_4/TiO_2$ for (A) wide spectra; (B) Co 2p; (C) C1s; (D) Zn 2p; (E) Ti 2p; and (F) O 1s, in accordance with the present invention.

FIGS. 7 (A-F)—depict UV-visible diffuse reflectance spectra of $TiO_2$, $ZnCo_2O_4$ and ZCOT; (B) Tauc plot for band gap calculation of $TiO_2$, $ZnCo_2O_4$ and ZCOT (ZT) samples; (C-D) Tauc plots for band gap calculation of TiO2, $ZnCo_2O_4$ and ZCOT (ZT) samples; (E) Mott-Schottky plots of $ZnCo_2O_4$; and (F) $N_2$ adsorption-desorption isotherms of $TiO_2$, ZCO and ZCOT samples, in accordance with the present invention.

FIGS. 8 (A-D)—depict (A) PL analysis of $TiO_2$ and $ZnCo_2O_4/TiO_2$ composite; (B) Nyquist plot of $TiO_2$, $ZnCo_2O_4$ and $ZnCo_2O_4/TiO_2$ composite; (C) EIS analysis of $ZnCo_2O_4/TiO_2$ composite; and (D) Cyclic voltammetry (CV) analysis of $TiO_2$, $ZnCo_2O_4$ and $ZnCo_2O_4/TiO_2$ composite, in accordance with the present invention.

FIGS. 9 (A-D)—depict (A) Effect of $ZnCo_2O_4$ loading on the performance of $TiO_2$ for photocatalytic CO2 reduction with $H_2O$ to CO and $CH_4$ in a batch photoreactor under visible light of 20 $mW/cm^2$; (B) Effect of UV and visible light irradiation on the performance of $ZnCo_2O_4/TiO_2$ composite for photocatalytic $CO_2$ reduction with $H_2O$; (C) Effect of UV and visible light irradiation on the performance of $ZnCo_2O_4/TiO_2$ composite for photocatalytic $CO_2$ reduction with $H_2O$; and (D) Proposed type II and Z-scheme heterojunction over ZnCo2O4/TiO2 composite under UV and visible light irradiation, in accordance with the present invention.

FIGS. 10 (A-D)—depict (A) Performance analysis of fixed bed and a monolith photoreactor for photocatalytic $CO_2$ reduction with $H_2O$ under UV-light; (B) Effect of reducing agent (methanol) on the performance of $ZnCo_2O_4/TiO_2$ composite in a monolith photoreactor under UV-light; (C) Stability analysis of $ZnCo_2O_4/TiO_2$ composite in a monolith photoreactor with methanol as the sacrificial reagent; and (D) Schematic illustration of efficiency enhancement in a monolith photoreactor, in accordance with the present invention.

FIGS. 11 (A-D)—depict (A) Photocatalytic $CO_2$ reduction to CO and $CH_4$ over ZCOT in a continuous flow photoreactor system; (B) Stability analysis of ZCOT in a multiple cycle; (C) EIS analysis of fresh and spent ZCOT composite; and (D) CV analysis of fresh and the spent ZCOT composite, in accordance with the present invention.

FIGS. 12 (A-B)—(A) Schematic interaction of $TiO_2$ and $ZnCo_2O_4$ for the charge transfer process; and (B) Schematic illustration of photocatalytic CO2 reduction to CO and $CH_4$ over $ZnCo_2O_4/TiO_2$ under visible and UV-light irradiation, in accordance with the present invention.

Figure 4:
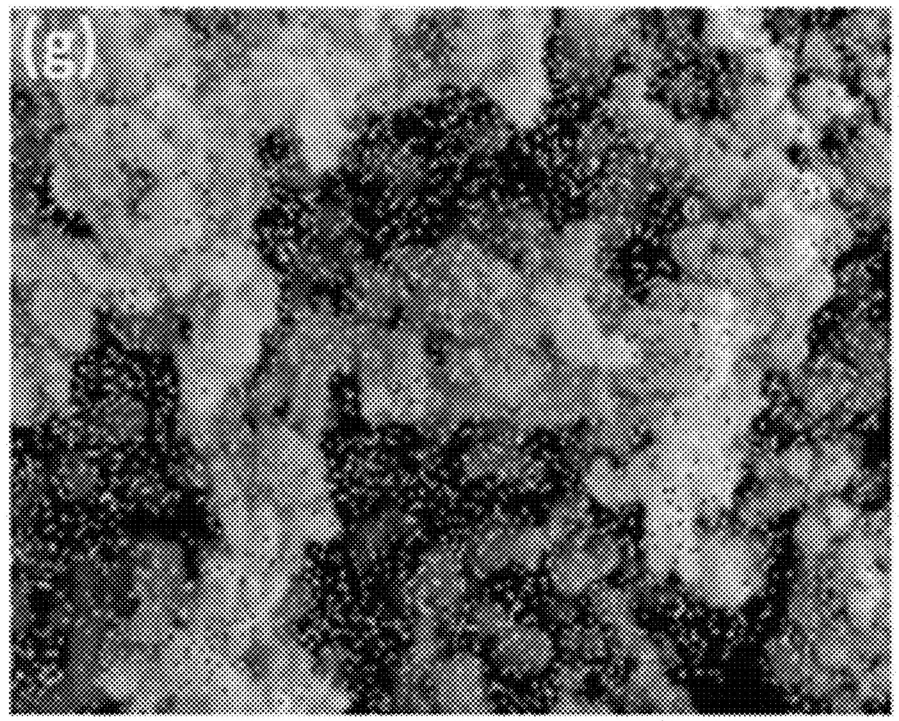
FIGS. 4 (A-K)—depict SEM images of (A) $TiO_2$, (B-C) $ZnCo_2O_4$, (D-F) $ZnCo_2O_4/TiO_2$; (G) SEM images of EDS mapping of $ZnCo_2O_4/TiO_2$ composite; (H) EDX spectrum of $ZnCo_2O_4/TiO_2$; and (I-K) Colour images of Co, Zn and Ti in the EDS spectrum of $ZnCo_2O_4/TiO_2$ composite, in accordance with the present invention.
Figure 4:
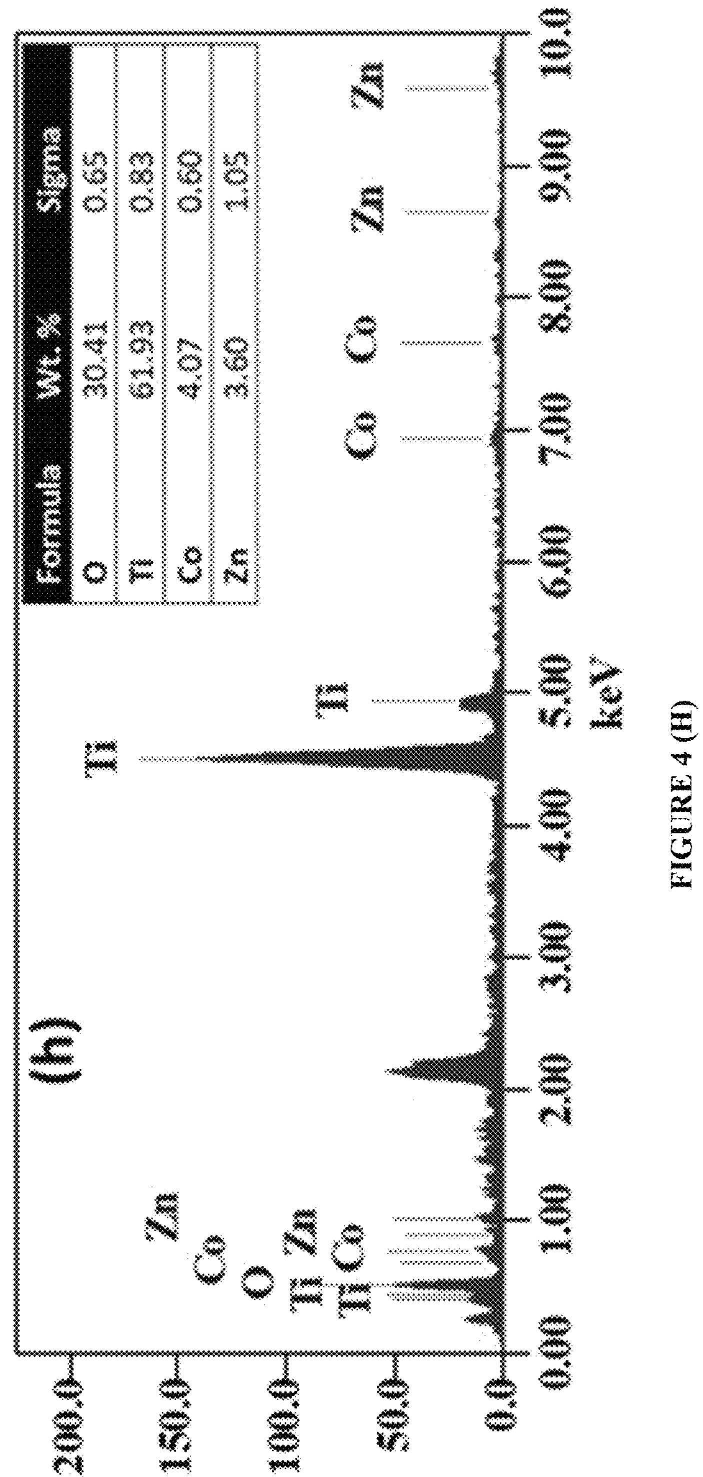

Reference is made to the accompanying figures throughout the specification, which form a part hereof, and which is shown by way of illustration specific embodiments by which the invention may be practiced. It is to be understood that other embodiments may be utilized and logical changes may be made without departing from the scope of the present invention. The following detailed description and examples, therefore, is not to be taken in a limiting sense, and the scope of the present invention is defined by the appended claims.

DETAILED DESCRIPTION

According to a first aspect of the present invention, there is provided a photocatalytic composite. The photocatalytic composite comprises zinc cobalt oxide nanorods ($ZnCo_2O_4$ NRs); and titanium dioxide ($TiO_2$), wherein said photocatalytic composite has a monolithic structure.

In some embodiments, the $ZnCo_2O_4$ NRs are one-dimensional (lD) nanorods of uniform size and shape.

In some embodiments, the $TiO_2$ is coupled to the zinc cobalt oxide nanorods ($ZnCo_2O_4$ NRs). For example, the $TiO_2$ may be present in the form of nanoparticles coupled to the zinc cobalt oxide nanorods ($ZnCo_2O_4$ NRs).

In some embodiments, the photocatalytic composite comprises $ZnCo_2O_4/TiO_2$. The $ZnCo_2O_4/TiO_2$ composite may be formed using a self-assembly approach.

In some embodiments, the photocatalytic composite comprises 1D/0D $ZnCoO_4/TiO_2$. In some embodiments, the photocatalytic composite consists of (e.g. consists essentially of) 1D/0D $ZnCoO_4/TiO_2$. In preferred embodiments, the photocatalytic composite is a monolithic $ZnCoO_4/TiO_2$ composite, preferably is a 1D/0D $ZnCoO_4/TiO_2$ composite.

As defined herein, a monolith is a substrate that supports a catalyst. In some embodiments, a monolith substrate may be present to provide the monolith structure. Any suitable monolithic substrate may be present to provide the monolith structure. For example, the monolith structure may be provided by a cordierite monolith. In some embodiments, a monolith substrate is present in the photocatalytic composite. In some embodiments, the monolithic structure is a honeycomb structure.

The monolith substrate may be in any suitable shape to provide the monolith structure. For example, the monolith substrate may be in a round shape of equal sizes, with a thickness of between 0.75 cm to 2.25 cm, and diameter of between 3 cm to about 9 cm. In a preferred embodiment, the monolith substrate has a round shape of equal sizes, with a thickness of between 1.40 cm to about 1.60 cm, and a diameter of between 5 cm to about 7 cm, more preferably with a thickness of 1.5 cm and a diameter of about 6 cm.

In some embodiments, the monolith substrate has a thickness of between 1.00 cm to 2.00 cm, preferably between 1.25 cm to 1.75 cm, more preferably between 1.40 cm to about 1.60 cm, even more preferably is about 1.5 cm. In some embodiments, the monolith substrate has a diameter of between 4 cm to about 8 cm, preferably between 5 cm to about 7 cm, more preferably of about 6 cm.

According to a third aspect of the present invention, there is provided the use of a photocatalytic composite according to the present invention for photocatalytic reduction of $CO_2$. The photocatalytic composite may be a photocatalytic composite according to the first aspect of the present invention.

According to a second aspect of the present invention, there is provided a method of manufacturing a monolithic $ZnCo_2O_4/TiO_2$ composite. The method comprises the steps of: obtaining $ZnCo_2O_4$ nanorods; obtaining a titanium dioxide sol-gel precursor; mixing the $ZnCo_2O_4$ nanorods and the titanium dioxide sol-gel precursor to form a $ZnCo_2O_4/TiO_2$ sol; obtaining a monolith substrate; and forming a monolithic $ZnCo_2O_4/TiO_2$ composite from the $ZnCo_2O_4/TiO_2$ sol and the monolith substrate using a sol-gel-dip coating method.

In some embodiments, the step of obtaining $ZnCo_2O_4$ nanorods comprises synthesising the $ZnCo_2O_4$ nanorods using a hydrothermal method. For example, the $ZnCo_2O_4$ nanorods may be synthesised from cobalt nitrate hexahydrate ($Co(NO_3)_2 \cdot 6H_2O$) and zinc acetate ($ZnC_4H_6O_4$), using any conventional hydrothermal method.

In some embodiments, the synthesis of $ZnCo_2O_4$ nanorods comprises the steps of: adding cobalt nitrate hexahydrate ($Co(NO_3)_2 \cdot 6H_2O$) and zinc acetate ($ZnC_4H_6O_4$) to water to form a precursor solution; adding urea, oxalic acid and ethanol to the solution to form a mixture; subjecting the mixture to thermal treatment to form particles; collecting the particles, washing the particles with ethanol and/or water and drying the particles; and subjecting the particles to thermal treatment to form the $ZnCo_2O_4$ nanorods. Any conventional method known in the art may be added or replace one or more of these steps.

In some embodiments, obtaining the titanium dioxide sol-gel precursor comprises the steps of: mixing titanium isopropoxide with 2-propanol to form a mixture; and hydrolysing the mixture by adding acetic acetic acid to form the titanium dioxide sol-gel precursor. Any conventional method known in the art may be added or replace one or more of these steps.

In some embodiments, a $ZnCo_2O_4/TiO_2$ composite is formed from the $ZnCo_2O_4/TiO_2$ sol using a self-assembly approach. The self-assembly process involves bringing together $ZnCo_2O_4$ and $TiO_2$under specific conditions to allow them to interact and form a composite material.

In some embodiments, the $ZnCo_2O_4$ nanorods are dispersed in 2-propanol before before mixing with the titanium dioxide sol-gel precursor to form the $ZnCo_2O_4/TiO_2$ sol.

In some embodiments, the the sol-gel-dip coating method comprises the steps of: dipping the monolith substrate into the $ZnCo_2O_4/TiO_2$ sol for a predetermined amount of time to form a coated monolith substrate; removing excess sol form the coated monolith substrate using hot compressed air and/or oven drying the coated monolith substrate; and subjecting the coated monolith substrate to a calcination process to form the monolithic $ZnCo_2O_4/TiO_2$ composite.

The steps involved with the sol-gel-dip coating method may be repeated one-five times (for example, repeated two-three times, preferably three times) to ensure uniform coverage of $ZnCo_2O_4/TiO_2$ on the surface of the monolith substrate.

In some embodiments, after obtaining the monolith substrate, the monolith substrate is: cut into round shapes of equal sizes, with a thickness of between 0.75 cm to 2.25 cm, and a diameter of between 3 cm to about 9 cm; cleaned using one or more of acetone, methanol or water; and dried.

In some embodiments, the monolithic substrate is cordierite monolith. The monolith substrate may be in any suitable shape to provide the monolith structure. For example, the monolith substrate may be in a round shape of equal sizes, with a thickness of between 0.75 cm to 2.25 cm, and diameter of between 3 cm to about 9 cm. In a preferred embodiment, the monolith substrate has a round shape of equal sizes, with a thickness of between 1.40 cm to about 1.60 cm, and a diameter of between 5 cm to about 7 cm, more preferably with a thickness of 1.5 cm and a diameter of about 6 cm.

In some embodiments, the monolith substrate has a thickness of between 1.00 cm to 2.00 cm, preferably between 1.25 cm to 1.75 cm, more preferably between 1.40 cm to about 1.60 cm, even more preferably is about 1.5 cm. In some embodiments, the monolith substrate has a diameter of between 4 cm to about 8 cm, preferably between 5 cm to about 7 cm, more preferably of about 6 cm.

In some embodiments, the monolithic $ZnCo_2O_4/TiO_2$ composite is a 1D/0D $ZnCo_2O_4/TiO_2$ composite.

According to a fourth aspect of the present invention, there is provided a method of photocatalytic reduction of $CO_2$ using a photocatalytic composite, comprising the steps of: obtaining a monolithic $ZnCo_2O_4/TiO_2$ composite; and reducing $CO_2$ using the monolithic $ZnCo_2O_4/TiO_2$ composite.

In some embodiments, the reduction is conducted with $H_2O$ in a fixed bed photoreactor, producing CO and $CH_4$ as main products.

In some embodiments, the reduction is conducted with $H_2O$ and methanol in a monolith photoreactor, yielding CO, $CH_4$, and $H_2$ as main products.

EXAMPLES

Chemicals and Materials

The chemicals utilized in this study include zinc acetate ($ZnC_4H_6O_4$), cobalt nitrate hexahydrate ($Co(NO_3)_2 \cdot 6H_2O$), urea ($CO(NH_2)_2$), oxalic acid ($C_2H_2O_4$), acetic acid, methanol, and titanium(IV) isopropoxide (TTIP, Sigma-Aldrich). The cordierite monoliths, with dimensions of 6 cm in diameter, 1.5 cm in length, and 200 channels per square inch, were supplied by Pingxiang Meitao Chemical Packing Co., Ltd., China.

Synthesis of $ZnCo_2O_4$ (ZCO)

A hydrothermal approach was used to synthesize $ZnCo_2O_4$ nanorods. A clear solution was prepared by continuously stirring 0.32 g of cobalt nitrate hexahydrate ($Co(NO_3)_2 \cdot 6H_2O$) and 0.2 g of zinc acetate ($ZnC_4H_6O_4$) in 20 mL of deionized water. In the next step, urea and oxalic acid in the prescribed amounts were added to the above solution. In the final step, ethanol was added to the above solution and it was stirred for an additional 30 minutes.

Subsequently, the mixture was transferred in a 50 mL Teflon-lined stainless steel reactor and heated to 140° C. for 12 hours. The material was centrifuged, cleaned with ethanol and water, and then allowed to dry in an oven to get the pink colour particles. The mixture was subsequently heated in a muffle furnace at 350° C. for two hours, resulting in the formation of $ZnCo_2O_4$ nanorods, characterized by their final blackish colour and named "ZCO". A comprehensive illustration of the hydrothermal synthesis of $ZnCo_2O_4$(ZCO) is shown in FIG. 1 (A).

Synthesis of Monolithic $ZnCo_2O_4/TiO_2$

A modified sol-gel method was used to synthesize the monolithic $ZnCo_2O_4/TiO_2$ composite. To prepare the titanium sol, 10 mL of titanium isopropoxide was mixed with 30 mL of 2-propanol and it was stirred for 30 minutes. Hydrolysis was then initiated by adding acetic acid (1 M) to the mixture. Separately, a predetermined amount of $ZnCo_2O_4$, dispersed in 2-propanol, was introduced into the solution. The resulting mixture was stirred for 6 hours, followed by continuous agitation for an additional 18 hours to form a thick $ZnCo_2O_4/TiO_2$ sol.

The monolithic samples were synthesized using a sol-gel-dip coating method. Initially, specific sizes of the monoliths with dimensions 1.5 cm thick and 6 cm in diameter with round shapes were cut and cleaned using acetone, methanol and water, respectively and oven-dried at 100° C. to get the clean monoliths for further use. In a dip-coating procedure, the monolith was slowly dipped into the $ZnCo_2O_4/TiO_2$ sol for five seconds and then it was removed and the excess sol attached was removed using hot compressed air. To ensure uniform coverage of the monolith surface with the sol, the procedure was repeated three times. After each cycle, the sol-coated monoliths were oven-dried at 100° C. for 24 hours. Following drying, the monoliths were calcined at 500° C. for two hours to ensure proper bonding and formation of the composite. The resulting material was named monolithic $ZnCo_2O_4/TiO_2$. To determine the amount of catalyst loaded onto the monolithic channels, the final weight of the monolith was measured and compared to its initial weight, with a net weight gain of approximately 150 mg of catalyst. A schematic representation of the synthesis process is shown in FIG. 1 (C).

Synthesis of $ZnCo_2O_4/TiO_2$ (ZCOT) (Also Referred to Herein as "ZT")

The synthesis of the $ZnCo_2O_4/TiO_2$ ("ZCOT") and $TiO_2$ powder samples followed a similar procedure to the synthesis of monolithic $ZnCo_2O_4/TiO_2$, but without coating the monolith surface. A schematic representation of the synthesis process is shown in FIG. 1 (B).

Characterization

X-ray powder diffraction (XRD) patterns of the pure and composite materials were obtained using a RIGAKU diffractometer. To examine the morphology and microstructures of the photocatalysts, high-resolution transmission electron microscopy (HRTEM) and field emission scanning electron microscopy (FESEM, JEOL 6010 PLUS/LA) were employed. The oxidation states and binding energies of the elements were analyzed using X-ray photoelectron spectroscopy (XPS) with a Thermo Scientific K-alpha+ instrument. UV-visible diffuse reflectance spectra (UV-Vis DRS) were collected using a Cary 100 Agilent Model G982 spectrometer, after loading powder samples into spheres. The surface area and pore size distribution were determined through $N_2$ adsorption-desorption isotherms. Charge separation efficiency was assessed using photoluminescence (PL) spectroscopy with a 325 nm laser, and the PL properties of the materials were analyzed using a HORIBA Scientific LabRAM HR Evolution system. Raman spectroscopy, conducted with a HORIBA Scientific Spectrophotometer (532 nm laser), was used to investigate the interactions between the composite components.

Electrocatalytic Tests

An electrochemical workstation (CS350, Wuhan) was employed to obtain data from electrochemical impedance spectroscopy (EIS) measurements. The experimental setup included a three-electrode configuration: a reference electrode (RE) of Ag/AgCl, a counter electrode (CE) made of Pt mesh, and a working electrode (WE) consisting of FTO glass. To prepare the working electrode, a slurry was first prepared by mixing 1 to 2 mL of N-methyl-2-pyrrolidone (NMP) with 0.15 g of conductive carbon, 0.05 g of polyvinylidene fluoride (PVDF), and 0.1 g of the catalyst material. This mixture was then carefully coated onto the FTO glass substrate, forming a uniform thin film. After coating, the electrode was dried at 80° C. for several hours to ensure proper adhesion and complete solvent evaporation. Once prepared, the working electrode was immersed in a 2M KOH electrolyte solution for the electrochemical tests. This setup was used to study the electrochemical properties of the catalyst and to evaluate its performance in processes such as charge transfer and impedance behaviour under various operating conditions.

Photoactivity Evaluation

The photocatalytic activity of $ZnCo_2O_4/TiO_2$ (ZCOT) and monolithic $ZnCo_2O_4/TiO_2$ (MZCOT) composite test in a cylindrical stainless steel photoreactor with a glass window for passing the light irradiation. The light sources used were 35W Xenon lamp (20 mW/cm2, $\lambda$=450 nm), 300 W Xenon (100 mW/cm2, $\lambda$=450 nm) and 200 W Hg lamp (100 mW/cm2, $\lambda$=354 nm). The reactor was connected to the mass flow controller of CO2, a water saturator to carry moisture and cooling fans to control the lamp and reactor temperature. In a typical procedure, a photocatalyst of 150 mg powder was distributed inside the reactor bottom surface which was directly exposed to light irradiation. In the case of the catalyst supported over the monolithic support, it was directly placed inside the middle of the reactor. Before starting the experiments, compressed $CO_2$ was circulated at a flow rate of 15 mL/min through the water container to saturate the catalyst surface with moisture. In the monolith photoreactor system, catalyst-coated monoliths were placed inside the reactor, maintaining identical operating conditions to those of the fixed-bed photoreactor system. For photocatalytic $CO_2$ reduction using methanol as a sacrificial reagent, 5 vol. % methanol was added to the water saturator. The resulting methanol/water vapours were carried by $CO_2$ gas before entering the reactor. All experiments were performed at ambient temperature and atmospheric pressure.

The products of the reaction were analyzed using a capillary column (Carboxen-1010 PLOT) coupled with a gas chromatograph equipped with both thermal conductivity detection (TCD) and flame ionization detection (FID) for accurate product evaluation. In the case of a continuous flow reactor system, high-purity $CO_2$ (5 mL/min) was continuously flowing through the bubbler containing 250 mL of methanol-water solution (5% methanol). The products were continuously injected into the GC after every 30-minute interval. Two TCD detectors, a stream selection valve (Valco 10 port), and Micro GC Fusion (INFICON) were incorporated when dealing with continuous flow and online product analysis. The CO, $CH_4$ and $H_2$ production rate and selectivity were calculated based on Eqs. (1) to (6). Eqs. (1) to (3) were used to determine CO, $CH_4$ and $H_2$ yield rates, whereas Eq. (4) to (6) were used to estimate the selectivity.

$$Y_{CO}(\mu\text{mol } g^{-1}h^{-1}) = \frac{2\times n\text{CO}}{\text{Weight}(g)\times\text{time}(h)} \quad (1)$$

$$Y_{CH_4}(\mu\text{mol } g^{-1}h^{-1}) = \frac{8\times n\text{CH}_4}{\text{Weight}(g)\times\text{time}(h)} \quad (2)$$

$$Y_{H_2}(\mu\text{mol } g^{-1}h^{-1}) = \frac{2\times n\text{H}_2}{\text{Weight}(g)\times\text{time}(h)} \quad (3)$$

$$S_{CO}(\%) = \frac{2\times n\text{CO}}{2\times n\text{CO}+8\times n\text{CH}_4+2\times n\text{H}_2}\times 100 \quad (4)$$

$$S_{CH_4}(\%) = \frac{8\times n\text{CH}_4}{2\times n\text{CO}+8\times n\text{CH}_4+2\times n\text{H}_2}\times 100 \quad (5)$$

$$S_{H_2}(\%) = \frac{2\times n\text{H}_2}{2\times n\text{CO}+8\times n\text{CH}_4+2\times n\text{H}_2}\times 100 \quad (6)$$

Results and Discussion

X-ray diffraction patterns (XRD) were used to examine the crystalline properties, and the results are displayed in FIG. 2 (A). The strong peaks at 2θ of 18.85°, 31.08°, 36.54°, 38.38°, 44.54°, 56.22°, 58.92° and 64.92°, linked with (111), (220), (311), (222), (400), (422), (511) and (440) crystal planes of $ZnCo_2O_4$. Notably, no impurity phases are detected, and similar observations were reported previously. The XRD patterns of $TiO_2$ show several 2θ peaks which are associated with (101), (004), (200), (105), (211), (204), (110) and (215) crystal planes of the anatase phase of $TiO_2$.

FIG. 2 (B) presents the Raman spectrum of $ZnCo_2O_4$ and the spectrum related to the ZCO shows peaks at 230.3 $cm^{-1}$, 481.2 $cm^{-1}$, 522.7 $cm^{-1}$, 694.1 $cm^{-1}$, and 774.1 $cm^{-1}$, corresponding to the phonon vibration modes of $F_{2g}$, $E_g$, $F_{2g}$, $F_{2g}$, and $A_{1g}$, respectively.

FIG. 2 (C) shows Raman spectra for $TiO_2$ and ZCOT samples. For the pure $TiO_2$, the Raman peaks appeared at 141.8, 197.2, 393.4, 512.4 and 635.1 $cm^{-1}$, which are related to $E_g$, $E_g$, $B_{1g}$, $A_{1g}/B_{1g}$, and $E_g$, respectively. The ZCOT composite reveals Raman peaks at 145.4, 198.9, 394.2, 513.3 and 638.7 $cm^{-1}$. The peak positions were moved towards higher values, indicating that the ZCO and $TiO_2$ had good interface contact throughout the construction of the ZCOT composite.

FIG. 2 (D) shows FTIR spectra of $TiO_2$, ZCO and ZCOT samples. The FTIR spectra of ZCO display a large peak, linked to hydroxyl molecules, between 3000 and 3600 $cm^{-1}$. The ZCOT composite exhibited all the characteristic peaks associated with both $TiO_2$ and $ZnCo_2O_4$ (ZCO), confirming the presence of both components in the composite material. All of these findings support the successful synthesis of the ZCOT composite using a simple self-assembly method, demonstrating its effective formation and integration of $TiO_2$ and $ZnCo_2O_4$ components.

The structure, shape, and morphology of the bare monolith are presented in FIG. 3 (A-D). FIG. 3 (A) illustrates the overall shape of the bare monolith, where a square-shaped structure divided by thin walls is visible. The surface of the bare monolith, as observed in FIG. 3(B), appeared rough and uneven due to the absence of the catalyst coating. Upon cutting the monolith cross-sectionally, a comparatively smooth surface was revealed, as depicted in FIG. 3 (C). Additionally, the morphology of the bare monolith surface is shown in FIG. 3 (D). Here, large particles with varying shapes are evident, which can likely be attributed to the $SiO_2^-Al_2O_3$ composition of the monolith material. These particles highlight the inherent texture and structural features of the bare monolith, emphasizing the differences introduced by the catalyst coating in subsequent analyses.

Furthermore, the shape and morphology of the monolith coated with the $ZnCo_2O_4/TiO_2$ catalyst are presented in FIG. 3 (E-H). FIG. 3(E) shows the square-shaped channels of the monolith, where a thin film of the coating material is visibly deposited. FIG. 3(F) demonstrates that the catalyst was uniformly and completely coated over the surface of the channels, ensuring consistent coverage. The SEM image in FIG. 3(G) provides a closer look at the coated surface, revealing a porous structure with small cracks. These features are attributed to the sol-gel coating process followed by annealing at high temperatures, which helped to enhance the adhesion and distribution of the catalyst. FIG. 3(H) further confirms the presence of both $ZnCo_2O_4$ and $TiO_2$ on the channel surface, validating the successful integration of the catalyst onto the monolith.

In summary, the structural and morphological analysis demonstrated the successful synthesis and coating of the $ZnCo_2O_4/TiO_2$ catalyst on the monolith surface. The bare monolith exhibited a rough and uneven surface with distinct particle shapes attributed to the $SiO_2$—$Al_2O_3$ composition. After coating, the catalyst was uniformly deposited as a thin film, with SEM analysis revealing a porous structure and good adhesion. The presence of $ZnCo_2O_4$ and $TiO_2$ was confirmed, highlighting the effectiveness of the sol-gel method and subsequent annealing process. These findings validate the development of a $ZnCo_2O_4/TiO_2$ monolithic composite with promising structural integrity and catalyst adherence.

The morphology and microstructure of $TiO_2$, $ZnCo_2O_4$ (ZCO), and the $ZnCo_2O_4/TiO_2$ (ZCOT) composite were thoroughly investigated using scanning electron microscopy (SEM), and the results are presented in FIG. 4. The SEM image in FIG. 4(A) shows the morphology of $TiO_2$, which is characterized by uniformly sized particles that tend to aggregate, forming noticeable clusters. FIGS. 4(B) and 4(C) display the morphology of $ZnCo_2O_4$, revealing a nanorods structure with uniform sizes and smooth surfaces enriched with microscopic pores, indicative of its porosity and structural uniformity. The morphology of the ZCOT composite is depicted in FIGS. 4(D-F), where $TiO_2$ is evenly distributed over the ZCO nanorods, forming a core-shell-like structure. This uniform distribution of $TiO_2$ is further highlighted in FIG. 4(F), which demonstrates a strong interaction between the two materials, with $TiO_2$ nanoparticles well-integrated into the composite. The energy dispersive spectrum (EDS) analysis in FIG. 4(G) confirms the distribution of Zn, Co, and Ti elements in the ZCOT composite. FIGS. 4(I-K) provide colour-coded elemental maps that further verify the presence and uniform distribution of Co, Zn, and Ti across the composite. FIG. 4(H) presents the EDS spectrum of ZCOT, which confirms the presence of O, Ti, Co, and Zn elements. The inset of FIG. 4(H) shows the elemental composition of ZCOT as 30.41% O, 61.93% Ti, 4.07% Co, and 3.60% Zn, confirming the expected stoichiometry of the composite. These observations highlight the successful synthesis of the ZCOT composite, characterized by a well-distributed core-shell structure, uniform morphology, and proper integration of $ZnCo_2O_4$ and $TiO_2$ components.

Transmission electron microscopy (TEM) was used to gain deeper insight into the morphology and structural characteristics of the $ZnCo_2O_4/TiO_2$ (ZCOT) composite. The TEM images, presented in FIG. 5, reveal detailed information on the size, shape, and distribution of the particles, as well as the interface between the $TiO_2$ and $ZnCo_2O_4$ components. FIG. 5(A) illustrates the 1D structure of $ZnCo_2O_4$ coated with $TiO_2$, demonstrating a well-defined interface and strong interaction between the two materials. FIG. 5(B) provides a closer view, showing that the $TiO_2$ nanoparticles are uniformly and completely encapsulated by $ZnCo_2O_4$.

This comprehensive coverage can be attributed to the self-assembly synthesis approach, which ensures the effective integration of the two materials. The method enhances both the structural uniformity and interaction between $ZnCo_2O_4$ and $TiO_2$, vital for achieving the desired catalytic and structural properties.

High-resolution TEM images in FIGS. 5(C-D) provide further evidence of the composite structural integrity. The high resolution images reveal a good interface between $ZnCo_2O_4$ and $TiO_2$, confirming the intimate contact and strong adhesion between the two components. These TEM findings validate the successful synthesis of the $ZnCo_2O_4/TiO_2$ composite with excellent structural and morphological characteristics, highlighting the effectiveness of the self-assembly approach in achieving a uniform and well-integrated composite material.

FIG. 6 shows X-ray photoelectron spectroscopy (XPS) of $ZnCo_2O_4/TiO_2$ composite. FIG. 6(A) shows wide spectra that confirm the presence of Zn, Co, Ti and O elements. FIG. 6(B) shows wide XPS spectra of Co 2p with binding energies 780.1, 782.0, 794.5 and 805 eV. The high-resolution spectra of C is are shown in FIG. 6(C), where four prominent peaks appeared with binding energy 284.4, 285.2, 286.1 and 288.3 eV, linked to C═C, C≡O, C—O and C═O, respectively. FIG. 6(D) shows high-resolution XPS spectra of Zn 2p with two main peaks positioned at 1021.5 and 1044.5 eV with energy separation of 23 eV, associated with the presence of Zn2+ oxidation. FIG. 6(E) displays the XPS spectra of Ti 2p, with binding energies at 458.2 and 463.4 eV, confirming the presence of titanium in the +4 oxidation state ($Ti^{4+}$), characteristic of $TiO_2$. In FIG. 6(F), the XPS spectra of O is reveal three peaks at binding energies of 529.4, 530.2, and 531.2 eV. These peaks are attributed to lattice oxygen (Zn—O, Co—O, Ti—O), oxygen vacancies, and adsorbed water molecules, respectively, providing valuable insights into the oxygen-related species present in the composite material.

UV-vis DRS spectra of $ZnCo_2O_4$, $TiO_2$ and ZCOT are presented in FIG. 7 (A). The UV-visible spectrum of $ZnCo_2O_4$ shows light absorbance in the wavelength range of 250-800 nm, which confirms its full spectrum optical properties with a substantial light absorbance capacity in the visible region. The $TiO_2$ shows light-harvesting capacity in the UV region with the band edge below 400 nm. Compared to pure $TiO_2$, the ZCOT exhibited increased light absorbance in the visible region. The band gap energy of 3.51 eV was obtained for $TiO_2$, as shown in FIG. 7(B). FIG. 7(C) shows the Tauc plot of $ZnCo_2O_4$ with the calculated band gap energy of 0.94 and 1.76 eV, respectively. In a previous work, a band gap of 1.67 eV was reported for the $ZNCo_2O_4$ QDs. A much lower band gap energy of ZCOT composite (3.12 eV) was obtained due to good interaction between the materials as shown in FIG. 7(D).

$ZnCo_2O_4$ is classified as an n-type semiconductor, as indicated by the linear relationships with positive slopes observed in FIG. 7(E). The flat band potential (Efb) of $ZnCo_2O_4$ was found to be −0.869 V. In n-type semiconductors, the conduction band (ECB) is typically 0.1-0.2 V lower than the flat band potential. By applying the formula ENHE=ESCE+0.24 V (NHE), the precise location of the conduction band for $ZnCo_2O_4$ was determined to be −0.62 V relative to the standard hydrogen electrode. Using the relationship EVB=Eg−ECB, the valence band (EVB) of $ZnCo_2O_4$ was calculated to be approximately 1.05 V. This information provides a deeper understanding of the electronic structure of $ZnCo_2O_4$, which is crucial for its performance in photocatalytic applications.

FIG. 7(F) presents the results of a nitrogen adsorption-desorption analysis conducted on $TiO_2$, ZCO, and ZCOT samples to investigate the textural characteristics of the as-prepared materials. All of the samples exhibited type IV isotherms with a hysteresis loop, which is indicative of mesoporous materials. This suggests that the materials possess a well-defined mesoporous structure, which is beneficial for applications such as catalysis and adsorption, where high surface area and porosity are crucial for performance. The BET surface area of $ZnCo_2O_4$ and $TiO_2$ was found to be 27 $m^2/g$ and 43 $m^2/g$, respectively. The ZCOT BET surface area of 23.54 $m^2/g$ was reported in earlier work, and this value nearly matches the one found in the most recent studies. On the other hand, a BJH surface area of 31 and 57 $m^2/g$ was observed. It could be observed that $TiO_2$ has a higher BET surface area, whereas, ZCO has a higher mesoporous structure as evidenced by BJH surface area. The BET surface area of the ZCOT was decreased to 15 $m^2/g$, whereas, the BJH surface area of 47 $m^2/g$ was achieved. In a different study, a BET surface area of 8.35 $m^2/g$ was reported for the pure $ZnCo_2O_4$, wheeras, it was increased to 52.8 m2/g for the $ZnCo_2O_4/g\text{-}C_3N_4$ composite. These results confirm that the ZCOT composite has a higher mesoporous structure than the pure $TiO_2$. Similarly, the pore volume of 0.0595 and 0.2585 $cm^3/g$ were obtained for the $TiO_2$ and ZCOT samples, whereas, the ZCOT composite shows a pore volume of 0.1140 $cm^3/g$ attained. All these results confirm the successful synthesis of ZCOT composite with higher mesoporosity due to the ZCO hierarchical nanotextures.

Table 1, set out below, shows the surface area and pore volume summary of $g\text{-}C_3N_4$, $ZnCo_2O_4$ and ZCOT composite samples.

TABLE 1

| Catalyst | BET ($m^2/g$) | BJH ($m^2/g$) | Pore volume ($cm^3/g$) |
|---|---|---|---|
| $TiO_2$ | 43 | 31 | 0.0595 |
| $ZnCo_2O_4$ | 27 | 57 | 0.2585 |
| $ZnCo_2O_4/TiO_2$ | 15 | 47 | 0.1140 |

The photoluminescence (PL) analysis of $TiO_2$ and $ZnCo_2O_4/TiO_2$ composites was carried out to evaluate the rate of electron transfer within these materials, with the corresponding results presented in FIG. 8(A). The electron transfer efficiencies of $TiO_2$, $ZnCo_2O_4$ NRs and ZCOT were further assessed through electrochemical impedance spectroscopy (EIS) measurements and the results are presented in FIG. 8(B). Nyquist plots of $ZnCo_2O_4$, $TiO_2$, and $ZnCo_2O_4/TiO_2$ composites display distinct semicircles. FIG. 8 (C) shows the Nyquist plot of $ZnCo_2O_4/TiO_2$ which may lead to two semicircle formations. The presence of two semicircles on a Nyquist plot indicates a system with distinct electrochemical phenomena occurring in different materials and their interfaces, enabling an effective charge transfer process.

FIG. 8(D) presents the cyclic voltammetry (CV) curves for $TiO_2$, $ZnCo_2O_4$, and the $ZnCo_2O_4/TiO_2$ composite, illustrating their electrochemical behaviours. Compared to $TiO_2$, $ZnCo_2O_4$ exhibited an increased charge-discharge area, indicating an enhanced capacity for charge storage and higher electrochemical activity. This enhancement suggests that $ZnCo_2O_4$ contributes significantly to improving the material's ability to facilitate redox reactions. Notably, the $ZnCo_2O_4/TiO_2$ composite displayed a further improvement, achieving higher oxidation and reduction potentials than its components. The enhanced redox behaviour of the composite suggests a synergistic interaction between $ZnCo_2O_4$ and $TiO_2$, which optimizes the electronic properties and facilitates more efficient charge separation and migration. Such an increase in oxidation/reduction potential is particularly advantageous for photocatalytic applications, as it can drive thermodynamically demanding reactions more effectively. Specifically, the higher potential observed for the $ZnCo_2O_4/TiO_2$ composite is beneficial for $CO_2$ reduction, enabling the activation and conversion of $CO_2$ molecules with greater efficiency. This highlights the potential of $ZnCo_2O_4/TiO_2$ composites as promising photocatalysts for applications in environmental remediation and sustainable energy production.

Photocatalytic CO2 Reduction in a Fixed Bed Photoreactor

The gas-phase $CO_2$ reduction reaction ($CO_2RR$) assisted by water vapour was employed to assess the photocatalytic (PC) efficiency of the as-synthesized catalysts. This evaluation was carried out both with and without the inclusion of a sacrificial electron donor. The presence of water vapour in the reaction environment facilitated the reduction of $CO_2$, while the sacrificial electron donor, when used, served to provide additional electrons, potentially enhancing the hotocatalytic performance by preventing charge carrier recombination. This setup allowed for a comprehensive analysis of the catalysts' efficiency in $CO_2$ conversion under different reaction conditions. To ensure the accuracy of the experimental results, several control tests were conducted before the photocatalytic experiments to validate the origin of the reaction products, specifically carbon monoxide (CO) and methane ($CH_4$). In the absence of light or the presence of light without a photocatalyst, no detectable quantities of CO or $CH_4$ were observed. In another control experiment, when $CO_2$ was substituted with helium (He), no photoinduced production of CO or $CH_4$ was detected. These observations strongly suggest that $CO_2$ serves as the primary reactant in the photocatalytic reduction process and that its conversion into CO and $CH_4$ is directly facilitated by the photocatalytic material under light illumination during the $CO_2RR$. These results confirm the crucial role of $CO_2$ as the carbon source in the generation of photocatalytic products.

The screening of $TiO_2$ and $ZnCo_2O_4$-loaded $TiO_2$ composites for photocatalytic reduction of $CO_2$ with $H_2O$ to produce CO and $CH_4$ was investigated using under 20 $mW/cm^2$ of visible light irradiation in a fixed bed photoreactor. This setup allowed for a detailed evaluation of the photocatalysts with a focus on their ability to reduce $CO_2$ effectively into valuable products, such as carbon monoxide (CO) and methane ($CH_4$). The experimental results, summarized in FIG. 9(*a*), reveal significant differences in product yields across the catalysts. For pristine $TiO_2$, the CO and $CH_4$ yields were 69.98 $mol \cdot g^{-1}$ and 28.00 $mol \cdot g^{-1}$, respectively. Comparatively, the $ZnCo_2O_4$ catalyst alone achieved lower yields, with CO and $CH_4$ production of 33.88 $mol \cdot g^{-1}$ and 35.60 $mol \cdot g^{-1}$, respectively. Interestingly, while $TiO_2$ exhibited superior performance in generating CO, $ZnCo_2O_4$ demonstrated a relatively higher yield of $CH_4$. This variation can be attributed to the difference in the reduction potentials of the catalysts and their ability to generate and transfer photoinduced charge carriers effectively under visible light.

When a composite of 5 wt. % $ZnCo_2O_4$ loaded onto $TiO_2$ (5% $ZnCo_2O_4/TiO_2$) was used, the CO and $CH_4$ production increased to 101.90 and 41.27 $mol \cdot g^{-1}$, respectively. This improvement is associated with enhanced charge carrier separation and transfer efficiency during the $CO_2$ reduction reaction. Optimization of the $ZnCo_2O_4$ loading to 10 wt. % (10% $ZnCo_2O_4/TiO_2$ composite) further boosted CO and $CH_4$ yields to 194.79 and 45.26 $mol \cdot g^{-1}$, respectively. The CO yield was 1.91, 2.78, and 5.70 times greater than that of 5% $ZnCo_2O_4/TiO_2$, pristine $TiO_2$, and pure $ZnCo_2O_4$, respectively, demonstrating the composite has superior performance in $CO_2$ photoreduction. On the other hand, the $CH_4$ yield over 10% $ZnCo_2O_4/TiO_2$ was 1.09, 1.27, and 1.62 times higher than that achieved with 5% $ZnCo_2O_4/TiO_2$, $ZnCo_2O_4$, and $TiO_2$, respectively. The enhanced $CH_4$ production with $ZnCo_2O_4$-containing composites can be attributed to the superior structural properties of $ZnCo_2O_4$, which promote prolonged electron lifetimes. Meanwhile, $TiO_2$ possess higher oxidation potential and facilitates efficient proton generation, thereby enhancing the photocatalytic activity. These insights highlight the critical role of $ZnCo_2O_4$ loading optimization in enhancing photocatalytic $CO_2$ reduction performance. This study highlights that while $ZnCo_2O_4$ promotes $CH_4$ production by extending electron lifetimes, $TiO_2$ is more effective for CO evolution due to its higher oxidation potential.

The photocatalytic performance of the optimized $10ZnCo_2O_4/TiO_2$ composite was comprehensively studied under different light irradiation conditions to evaluate its efficiency in reducing $CO_2$ into valuable products, specifically carbon monoxide and methane. The experiments involved visible light irradiance at intensities of 20 mW $cm^{-2}$ and 100 mW $cm^{-2}$ and UV light irradiance at 100 mW $cm^{-2}$. The results of CO and $CH_4$ production under these conditions are depicted in FIGS. 9 (A-C). The trends for CO and $CH_4$ production were continuous with the visible light irradiation, however, their production was first increased and then decreased when the UV-light was employed. As illustrated in FIG. 9 (D), this behavior is explained by the formation of a type-II heterojunction between $ZnCo_2O_4$ and $TiO_2$ under visible light conditions. The type-II heterojunction enhances charge separation and promotes more efficient charge transfer, leading to the preferential formation of $CH_4$ at higher light intensities.

Under UV light irradiation at an intensity of 100 mW $cm^{-2}$, the composite demonstrated a significant increase in the production of both CO and $CH_4$. This phenomenon is linked to the increased penetration depth of the UV light over the fixed bed catalyst, which generates a higher density of photogenerated charge carriers. Furthermore, the enhanced performance under UV light is attributed to the establishment of a Z-scheme heterojunction within the $ZnCo_2O_4/TiO_2$ composite. The Z-scheme heterojunction enhances photocatalytic efficiency by retaining the strong oxidative potential of the photogenerated holes in $TiO_2$ and the strong reductive potential of the photogenerated electrons in $ZnCo_2O_4$. This configuration facilitates efficient charge carrier separation and supports the generation of a higher number of protons, which are essential for $CO_2$ reduction. The superior redox capabilities of the Z-scheme system result in the concurrent enhancement of CO and $CH_4$ production under UV light conditions.

Photocatalytic CO2 Reduction in a Monolith Photoreactor

The performance of photocatalytic systems can be significantly influenced by both the type of photoreactor and the reducing agents employed. In this study, the efficiency of a $10ZnCo_2O_4/TiO_2$ composite was systematically evaluated under UV-light irradiation using two different photoreactor configurations: a fixed-bed photoreactor and a monolith photoreactor.

The results, illustrated in FIG. 10(A), highlight distinct differences in the catalytic outcomes between these setups. In the fixed-bed photoreactor, lower yields of CO and $CH_4$ were observed, with a progressive decline in their production over irradiation time. Conversely, the monolith photoreactor demonstrated superior performance, delivering higher and more sustained production rates. The maximum CO yield achieved in the monolith photoreactor was 679.3 $\mu mol\ g^{-1}$, which represents a 4.37-fold increase compared to the fixed-bed system under identical conditions for photocatalytic $CO_2$ reduction with $H_2O$. The enhanced performance of the monolith photoreactor is attributed to its unique structural advantages, including a significantly larger available surface area within the monolith channels. This facilitates more efficient light harvesting and promotes surface reactions, thereby optimizing the photocatalytic process. These findings underscore the critical role of reactor design in improving the efficacy of photocatalytic systems for $CO_2$ reduction.

The performance of the $10ZnCo_2O_4/TiO_2$ composite was further evaluated in a monolith photoreactor, using methanol as a sacrificial reagent. The results of this investigation are presented in FIG. 10(B). The addition of methanol, as a sacrificial electron donor, plays a crucial role in improving photocatalytic efficiency by providing additional electrons to prevent the recombination of photogenerated charge carriers. This enhances the overall photocatalytic reduction of $CO_2$, leading to increased product yields. The data in FIG. 10(B) highlights the effectiveness of the 10 $ZnCo_2O_4/TiO_2$ composite in the presence of methanol, demonstrating its potential for efficient $CO_2$ reduction under practical reaction conditions. When methanol was employed in the photocatalytic $CO_2$ reduction process, hydrogen ($H_2$) emerged as the primary product, accompanied by minor amounts of $CH_4$ and CO. Notably, in contrast to using water alone, where $H_2$ production was undetectable, the introduction of methanol facilitated the generation of 66,330 $\mu mol\ g^{-1}$ of $H_2$. Furthermore, the production of CO and $CH_4$ in the monolith photoreactor using the methanol-water mixture was 19.8 and 111.3 times greater, respectively, than that achieved using only water for $CO_2$ reduction. These factors collectively contribute to the superior photocatalytic performance observed in the monolith photoreactor system.

The stability of the $ZnCo_2O_4/TiO_2$ composite was further assessed in a monolith photoreactor using methanol as a sacrificial reagent, and the results are depicted in FIG. 10(C). Throughout three consecutive photocatalytic cycles, the system exhibited distinct trends in product generation.

A schematic illustration of the performance of a monolith photoreactor is presented in FIG. 10(D). In this system, the photocatalyst is uniformly coated along the inner walls of the monolith channels, forming a thin film that facilitates efficient attachment of reactants to the catalyst surface. This configuration minimizes diffusion limitations by promoting closer interaction between the reactants and the active catalytic sites. Consequently, the reaction predominantly shifts towards a surface-limited regime, where the reaction rate is directly proportional to the concentration of reactants on the catalyst surface. The structural design of the monolith channels also plays a crucial role in enhancing light penetration. These channels act as pathways that allow light to reach deeper regions of the catalyst, thereby maximizing light utilization during the photocatalytic process. This optimized light harvesting is critical for generating the photoinduced charge carriers (electrons and holes) necessary for the photocatalytic reactions. Moreover, the monolith photoreactor design promotes a synergistic interaction among the catalyst, reactants, and light irradiation. This enhanced interaction reduces the recombination of charge carriers, ensuring their efficient utilization in driving the photocatalytic reactions. Such a configuration not only improves the overall reaction kinetics but also enhances the quantum efficiency of the system. These features collectively highlight the advantages of monolith photoreactors in achieving superior photocatalytic performance compared to traditional reactor designs.

Photocatalyitc CO2 Reduction in a Continuous Photoreactor

A continuous-flow fixed-bed photoreactor system was employed to further evaluate the efficacy of the $ZnCo_2O_4/TiO_2$ composite for photocatalytic $CO_2$ reduction. The reaction was conducted using a methanol-water mixture under UV light irradiation. This setup provided a dynamic and controlled environment, allowing for a more realistic assessment of the composite performance over extended periods. The methanol-water mixture acted as a sacrificial electron donor, enhancing the photocatalytic reduction process by providing additional electrons to facilitate $CO_2$ conversion. In this setup, a 5 mL/min flow of $CO_2$ gas was continuously bubbled into a 5% methanol-water solution before entering the photoreactor. The reactor was equipped with an online gas chromatography system for real-time analysis of the products. The primary products identified were CO and $H_2$, with trace amounts of $CH_4$, as shown in FIG. 11(A). According to the findings, the rates of CO and $H_2$ production rose gradually throughout the irradiation period until they reached a maximum value, at which point they stabilized at a steady-state rate. Using methanol as a sacrificial reagent significantly enhanced the overall product yields. This enhancement is attributed to the increased generation of charge carriers (photoinduced electrons and holes) and protons, which facilitated the activation of the $CO_2$ reduction reaction. These findings highlight the advantages of continuous-flow photoreactors for real-time product analysis and sustained catalytic performance under dynamic operating conditions.

The performance of the ZnCo2O4/$TiO_2$ composite was further conducted in consecutive three cycles and the results are shown in FIG. 11(B). In all three cycles, the highest yield of CO and $H_2$ were produced and their production was continuous over the irradiation time. In all three cycles, the highest and continuous yield of CO and $H_2$ was obtained, whereas the production of $CH_4$ was somewhat increased. These results confirm a higher efficient and stable $ZnCo_2O_4/TiO_2$ composite to produce synthesis gas during photocatalytic $CO_2$ reduction with a methanol/water mixture under UV-light irradiation.

The spent catalyst was further assessed using Electrochemical Impedance Spectroscopy (EIS) and Cyclic Voltammetry (CV) analysis, with the results presented in FIG. 11 (C-D). The EIS plots of the fresh and spent $ZnCo_2O_4/TiO_2$ composites are shown in FIG. 11 (C), revealing distinct trends between the two samples. For the fresh composite, the EIS plot exhibited a lower semicircle, which indicates lower charge transfer resistance and higher photocatalytic efficiency. In contrast, the EIS plot of the spent catalyst displayed a different trend, likely reflecting an increase in resistance due to changes in the material's surface properties or structure during the reaction process. These differences highlight the impact of prolonged use on the catalyst's performance and provide insights into its stability and potential for reuse. All these findings confirm good stability and the efficiency of the composite to provide a continuous photocatalytic efficiency during the CO2 reduction process.

Performance Analysis

The performance of ZCOT in terms of production rate and selectivity for CO, $CH_4$, and $H_2$ production was systematically compared across different experimental setups, including variations in light sources, reactor types (e.g., fixed bed and monolith reactors), and reducing agents such as methanol and the results are summarized in Table 2. Using a fixed bed photoreactor operated in batch mode with a $CO_2$—$H_2$ system under visible light irradiation, production rates of CO and $CH_4$ were measured at 300.8 and 898.4 μmol $g^{-1}$ $h^{-1}$, with selectivities of 25.1% and 74.9%, respectively. In contrast, a monolith photoreactor under similar batch mode conditions yielded production rates of 679.4 and 799.2 μmol $g^{-1}$ $h^{-1}$ for CO and $CH_4$, with selectivities of 45.9% and 54.1%, respectively. These findings indicate that the monolith photoreactor is more effective for CO production, achieving higher yield and selectivity for this product. Conversely, the fixed bed photoreactor demonstrated superior performance for $CH_4$ production under identical operating conditions. This distinction highlights the critical influence of reactor configuration on the product distribution and efficiency of photocatalytic $CO_2$ reduction.

The performance of the monolith photoreactor in batch mode was further evaluated using two types of light sources and employing methanol and water as reducing agents. When UV light was utilized with water as the reducing agent, production rates of CO and $CH_4$ reached 1358.6 and 1755.2 μmol $g^{-1}$ $h^{-1}$, respectively. These values were 1.99 and 2.196 times higher than those achieved under visible light irradiation. This significant enhancement was attributed to the superior penetration capability of UV light into the monolith channels and the formation of a Z-scheme heterojunction, which effectively maximized the oxidation and reduction potentials. Regarding selectivity, the type of light source had a minimal impact on the selectivity of CO and $CH_4$. However, UV light slightly increased the $CH_4$ selectivity from 54.1% under visible light to 56.7%. Notably, in all reactor systems tested with water as the reducing agent, no detectable production of hydrogen was observed. These findings highlight the crucial role of light source wavelength and reactor design in optimizing the efficiency and selectivity of photocatalytic $CO_2$ reduction processes.

The performance of the monolith photoreactor in batch mode under UV light was further investigated using a methanol-water mixture as the reducing agent. This setup achieved the highest production rates of CO, $CH_4$, and $H_2$ at 26,908, 195,336, and 132,658 μmol $g^{-1}$ $h^{-1}$, with selectivities of 7.6%, 55.5%, and 37.4%, respectively. Notably, the inclusion of methanol significantly enhanced $H_2$ production, which was absent when water alone was used as the reducing agent. Additionally, the production rates of CO and $CH_4$ with the methanol-water mixture were 19.8 and 111.3 times higher, respectively, compared to those obtained during $CO_2$ reduction using water alone. These results reveal methanol's effectiveness as a reducing agent, attributed to its ability to generate additional protons and reduce charge recombination rates, thereby maximizing the production efficiencies of CO, $CH_4$, and $H_2$. This highlights the potential of methanol-water systems to optimize photocatalytic $CO_2$ reduction processes.

Using a fixed bed photoreactor and a methanol-water mixture, the ZCOT composite performance was further assessed in a continuous flow system. Notably, the production of CO was the highest among the products, accompanied by a significant amount of $H_2$, while $CH_4$ production was comparatively low. The production rates of CO, $CH_4$, and $H_2$ were 6054, 264, and 2234 μmol $g^{-1}$ $h^{-1}$, respectively, with selectivities of 70.8%, 3.1%, and 26.1%. These findings suggest that during the photocatalytic $CO_2$ reduction with the methanol-water mixture, CO is initially produced as the primary product. Over prolonged residence times on the photocatalyst surface, CO may undergo further conversion to $CH_4$. The observed production of hydrogen can be attributed to the activation of the methanol-reforming reaction, which facilitates the generation of hydrogen in significant quantities. This highlights the potential of the ZCOT composite in continuous flow systems for tailored product selectivity in photocatalytic applications.

The comparative analysis highlights that the choice of reactor type, light source, and reducing agent significantly influences product distribution in photocatalytic $CO_2$ reduction. Fixed bed reactors are more suitable for $CH_4$ production, while monolith reactors excel in CO production under batch conditions. The use of methanol as a reducing agent with UV light dramatically improves hydrogen and hydrocarbon production due to enhanced charge separation and proton availability. In continuous flow systems, CO dominates as the primary product, with potential pathways for further conversion to $CH_4$ over extended reaction times. These findings underscore the versatility and tunability of ZCOT composites for targeted photocatalytic applications.

TABLE 2

Summary of performance comparison of reactors, light source and reducing agent on photocatalytic CO2 reduction

| Catalyst | Parameters (Reactor, light source, process type) | Yield rate (μmol·$g^{-1}$·$h^{-1}$) | | | Selectivity (%) | | |
|---|---|---|---|---|---|---|---|
| | | $Y_{CO}$ | $Y_{CH4}$ | $Y_{H2}$ | $S_{CO}$ | $S_{CH4}$ | $S_{H2}$ |
| $10ZnCo_2O_4$ | Fixed bed, Visible light, Batch, $H_2O$ | 300.8 | 898.4 | 0 | 25.1 | 74.9 | 0 |
| $10ZnCo_2O_4$ | Monolith, Visible light, Batch, $H_2O$ | 679.4 | 799.2 | 0 | 45.9 | 54.1 | 0 |
| $10ZnCo_2O_4$ | Monolith, UV-light, Batch, $H_2O$ | 1358.6 | 1755.2 | 0 | 43.6 | 56.7 | 0 |
| $10ZnCo_2O_4$ | Monolith. UV-light, Batch, SMeOH—$H_2O$ | 26908 | 195336 | 132658 | 7.6 | 55.0 | 37.4 |
| $10ZnCo_2O_4$ | Fixed bed, UV-light, continuous, Flow = 5 mL/min. 5MeOH—$H_2O$ | 6054 | 264 | 2234 | 70.8 | 3.1 | 26.1 |

Proposed Mechanism

The mechanisms underlying the photocatalytic activity of the ZnCo2O4/TiO2 composite are schematically illustrated in FIG. 12(A) illustrates the interaction between 0D $TiO_2$ particles and the 1D $ZnCo_2O_4$ structure. In this arrangement, the $TiO_2$ particles are embedded within the one-dimensional framework of $ZnCo_2O_4$, facilitating robust interfacial interactions. This configuration not only enhances the physical integration of the two materials but also creates highly efficient charge transfer pathways. Moreover, the inherent properties of the 1D structure play a critical role in improving photocatalytic performance. The one-dimensional electron transfer along the $ZnCo_2O_4$ framework promotes prolonged charge carrier lifetimes by reducing charge recombination. This reduced recombination significantly boosts the photocatalytic efficiency, as it allows more photogenerated charges to participate in catalytic reactions rather than being lost. Overall, the synergistic interaction between OD $TiO_2$ and 1D $ZnCo_2O_4$ provides a promising approach for enhancing charge transfer dynamics and optimizing photocatalytic activity.

For photocatalytic $CO_2$ reduction, type II and Z-scheme heterojunction production under visible and UV light irradiation is depicted in FIG. 12(B). Under visible light irradiation, the type-II heterojunction directs photogenerated electrons and holes to separate components, enabling charge separation but reducing the driving force for redox reactions. In contrast, UV light irradiation induces the formation of a Z-scheme heterojunction, which aligns the energy bands of $ZnCo_2O_4$ and $TiO_2$ to maximize oxidation and reduction potentials. This alignment significantly enhances the separation and utilization of photogenerated charge carriers, resulting in higher yields of CO and $CH_4$. The reaction involved for the reduction of $CO_2$ and oxidation of water/methanol to produce CO, CH4 and H2 is presented in Eq. (7) to (13):

$$TiO_2 + h\nu \rightarrow TiO_2(e^-_{CB}) + TiO_2(h^+_{VB}) \quad (7)$$

$$ZnCo_2O_4 + h\nu \rightarrow ZnCo_2O_4(e^-_{CB}) + ZnCo_2O_4(h^+_{VB}) \quad (8)$$

$$2H_2O + 4h^+ \rightarrow 4h^+ + O_2 \quad (9)$$

$$CO_2 + e^- \rightarrow \bullet CO^- \quad (10)$$

$$\bullet CO^- + 2H^+ + e^- \rightarrow CO + H_2O \quad (11)$$

$$\bullet CO^- + 8H^+ + 7e^- \rightarrow CH_4 + 2H_2O \quad (12)$$

$$4H^+ + 4e^- \rightarrow 2H_2 \quad (13)$$

The two-electron pathway for CO production is dominant under visible light due to limited redox potential. The eight-electron pathway for $CH_4$ formation is favoured under UV light, supported by efficient charge separation and strong redox potential in the Z-scheme configuration. Type-II heterojunctions are effective for moderate charge separation but limit multi-electron reduction processes. Z-scheme heterojunctions combine the best of both components' redox capabilities, enabling higher yields and selectivity for more complex reduction products. Using a monolith photoreactor, the photocatalytic activity for $CO_2$ reduction was increased due to the efficient utilization of light irradiation and effective adsorption-desorption process over the thin film of the catalyst surface. Similarly, continuous flow photoreactor confirms that $CO_2$ was first converted to CO before being converted to $CH_4$ in a batch mode fixed bed photoreactor system.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

It will be appreciated by persons skilled in the art that the above embodiment(s) have been described by way of example only and not in any limitative sense, and that various alterations and modifications are possible without departing from the spirit and scope of the invention as defined by the appended claims. Various modifications to the detailed designs as described above are possible.

The invention claimed is:

1. A photocatalytic composite comprising:

zinc cobalt oxide nanorods ($ZnCo_2O_4$ NRs); and titanium dioxide ($TiO_2$), wherein the $ZnCo_2O_4$ NRs are present at 5 to 10 wt. % relative to the $TiO_2$, wherein said photocatalytic composite has a monolithic structure.

2. The photocatalytic composite according to claim 1, wherein the $ZnCo_2O_4$ NRs are nanorods having an elongated structure with a length greater than their width and height, wherein the nanorods are of uniform size and shape.

3. The photocatalytic composite according to claim 1, wherein $TiO_2$ nanoparticles are coupled to the zinc cobalt oxide nanorods ($ZnCo_2O_4$ NRs).

4. The photocatalytic composite according to claim 1, wherein the $TiO_2$nanoparticles are uniformly distributed over the $ZnCo_2O_4$ nanorods forming a core-shell-like structure.

5. The photocatalytic composite according to claim 1, wherein the $ZnCo_2O_4$ nanorods have an elongated rod-like structure and the $TiO_2$ nanoparticles are coupled to the $ZnCo_2O_4$ nanorods.

6. The photocatalytic composite according to claim 1, wherein the monolithic structure is a honeycomb structure.

* * * * *